(12) United States Patent
Okazawa

(10) Patent No.: US 7,833,975 B2
(45) Date of Patent: Nov. 16, 2010

(54) PROPHYLACTIC/THERAPEUTIC AGENT FOR NEURODEGENERATIVE DISEASE

(75) Inventor: Hitoshi Okazawa, Tokyo (JP)

(73) Assignee: National University Corporation Tokyo Medical and Dental University, Tokyo (JP)

( * ) Notice: Subject to any disclaimer, the term of this patent is extended or adjusted under 35 U.S.C. 154(b) by 0 days.

(21) Appl. No.: 12/313,837

(22) Filed: Nov. 25, 2008

(65) Prior Publication Data

US 2009/0280488 A1 Nov. 12, 2009

Related U.S. Application Data

(63) Continuation of application No. PCT/JP2007/058873, filed on Apr. 24, 2007.

(30) Foreign Application Priority Data

Jun. 1, 2006 (JP) .............................. 2006-154059

(51) Int. Cl.
- C07K 1/00 (2006.01)
- C07K 14/00 (2006.01)
- C07K 38/16 (2006.01)
- C07K 38/17 (2006.01)

(52) U.S. Cl. .................. 514/8.3; 514/1.1; 514/21.2; 530/350; 530/358

(58) Field of Classification Search ............... None
See application file for complete search history.

(56) References Cited

U.S. PATENT DOCUMENTS 7,288,250 B2 * 10/2007 Newman et al. ......... 424/133.1
2006/0084072 A1   4/2006 Muchowski

FOREIGN PATENT DOCUMENTS

| JP | 2003-267874 | 9/2003 |
| WO | 2004/061456 | 7/2004 |
| WO | 2005/025604 | 3/2005 |

OTHER PUBLICATIONS

Takata, Kazuyuki et al, Role of High Mobility Group Protein-1 (HMG1) in amyloid-β homeostasis, Biochemical and Biophysical Research Communications, 2003, vol. 301, No. 3, p. 699-703.
Agresti, Alessandra et al, HMGB Proteins and Gene Expression, Current Opinion in Genetics & Development, 2003, vol. 13, No. 2, p. 170-178.
Travers, Priming the Nucleosome: A Role for HMGB Proteins?, European Molecular Biology Organization, EMBO Reports, vol. 4, No. 2, 2003, p. 131-136.
Alpha-synuclein filaments bind the transcriptional regulator HMGB-1, Lindersson, E. et al, Neuroreport, vol. 15, No. 18, Dec. 22, 2004, pp. 2735-2739. XP008114956.
Dangerous liaisons: polyglutamine meets HMGB, Todi, S. et al., Nature Cell Biology, vol. 9, No. 4, Apr. 2007, pp. 359-361. XP002555670.

Proteome analysis of soluble nuclear proteins reveals that HMGB1/2 suppress genotoxic stress in polyglutamine diseases, Qi, M. et al, Nature Cell Biology, vol. 9, No. 4, Apr. 2007, pp. 402-414, Supplementary Information pp. 1-7 with Supplementary Methods (3 pages). XP002555671.
Proteome analysis of soluble nuclear proteins links genotoxic stress to the polyglutamine disease pathology, Okazawa, H., Abstracts/Neuroscience Research, Elsevier, Shannon, IR, vol. 58, Jan. 1, 2007, pp. S16. XP022174779.
Polyglutamine diseases: a transcription disorder?, Okazawa, H., CMLS Cellular and Molecular Life Sciences, vol. 60, No. 7, Jul. 1, 2003, pp. 1427-1439. XP003006820.
Polyglutamine and CBP: fatal attraction?, McCampbell, A. et al., Nature Medicine, vol. 7, No. 5, May 2001, pp. 528-530. XP002555674.
Polyglutamine disease: acetyltransferases awry, Hughes, Current Biology, vol. 12, No. 4, Feb. 19, 2002, pp. R141-R143. XP009116273.
Expanded polyglutamine stretches lead to aberrant transcriptional regulation in polyglutamine diseases, Shimohata, T. et al, Human Cell, vol. 14, No. 1, Mar. 1, 2001, pp. 17-25. XP008114385.
To the 30-nm chromatin fiber and beyond, Adkins et al., Biochimica et Biophysica Acta. Gene Structure and Expression, Elsevier, Amsterdam, NL, vol. 1677, No. 1-3, Mar. 15, 2004, pp. 12-23. XP004496566.
Suppression of polyglutamine-induced toxicity in cell and animal models of Huntington's disease by ubiquilin, Wang, H. et al., Human Molecular Genetics, vol. 15, No. 6, Mar. 2006, pp. 1025-1041. XP002555672.
Mutant huntingtin alters MAPK signaling pathways in PC12 and striatal cells: ERK1/2 protects against mutant huntingtin-associated toxicity, Apostol, B. et al., Human Molecular Genetics, vol. 15, No. 2, Jan. 2006, pp. 273-285. XP002555673.
Transcriptional repression and cell death induced by nuclear aggregates of non-polyglutamine protein, Fu, L. et al, Neurobiology of Disease, vol. 20, No. 3, Dec. 1, 2005, pp. 656-665. XP005153852.

* cited by examiner

*Primary Examiner* — Olga N Chernyshev
(74) *Attorney, Agent, or Firm* — Carmody & Torrance LLP

(57) ABSTRACT

To provide a prophylactic/therapeutic agent for neurodegenerative diseases (such as polyglutamine diseases), the agent containing an HMGB family protein or a derivative thereof, such as a protein according any one of (a) and (b) below:

(a) a protein having the amino acid sequence of SEQ ID NO: 2, 4, 6 or 8; and (b) a protein having an amino acid sequence resulting from deletion, substitution, addition or insertion of one or more amino acids in the amino acid sequence of SEQ ID NO: 2, 4, 6 or 8 and having binding activity to an abnormal polyglutamine protein produced in a neurodegenerative disease.

1 Claim, 13 Drawing Sheets

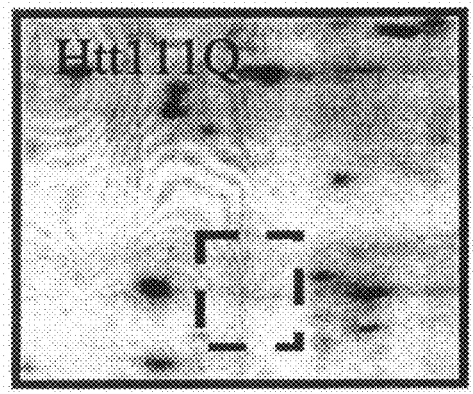
Fig. 2A
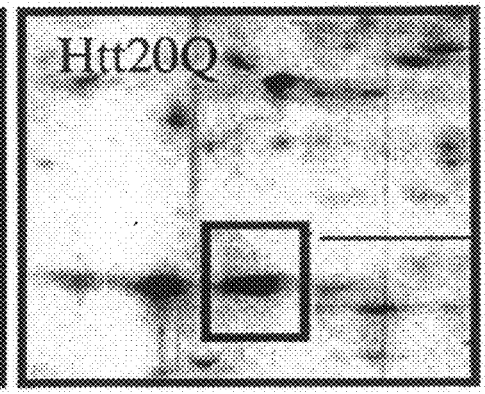
Fig. 2B
Fig. 3A
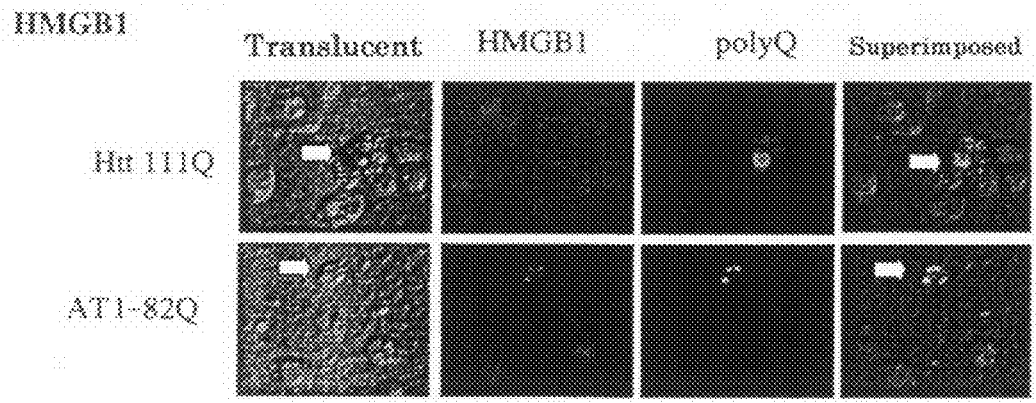
Fig. 3B
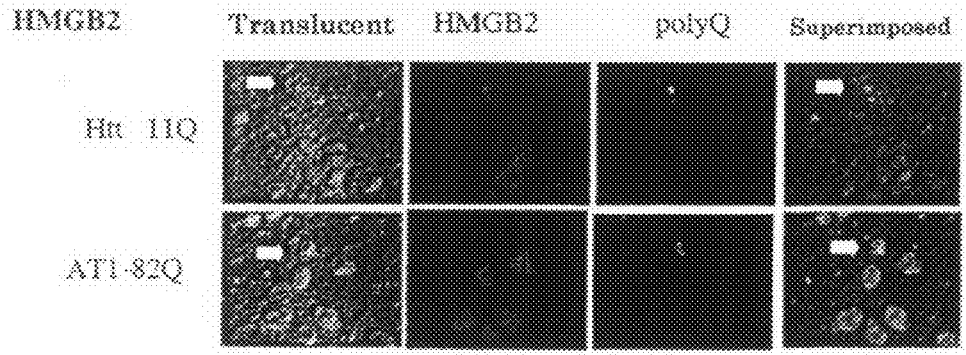

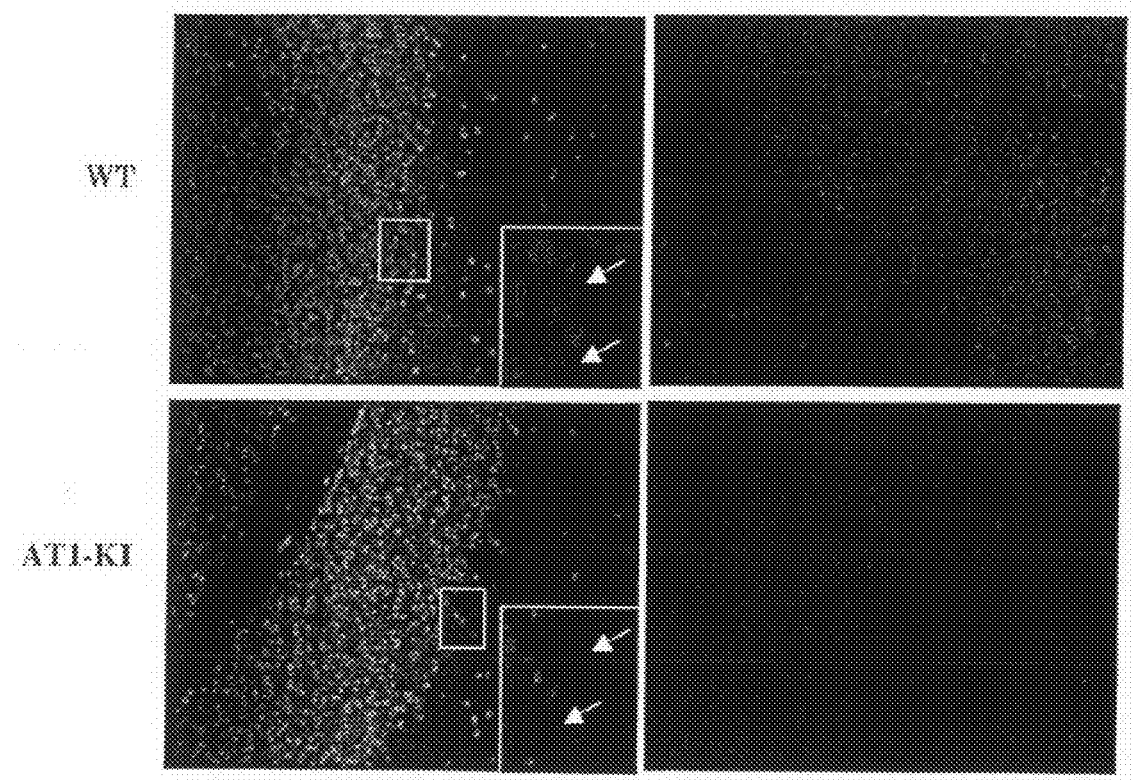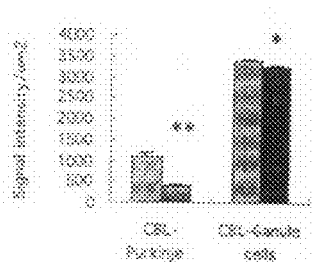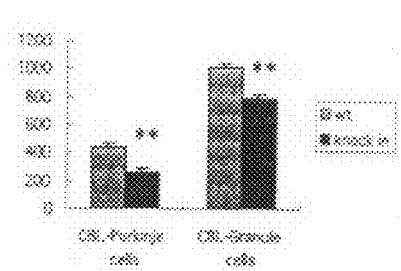

WB for assays with Purkinje cells

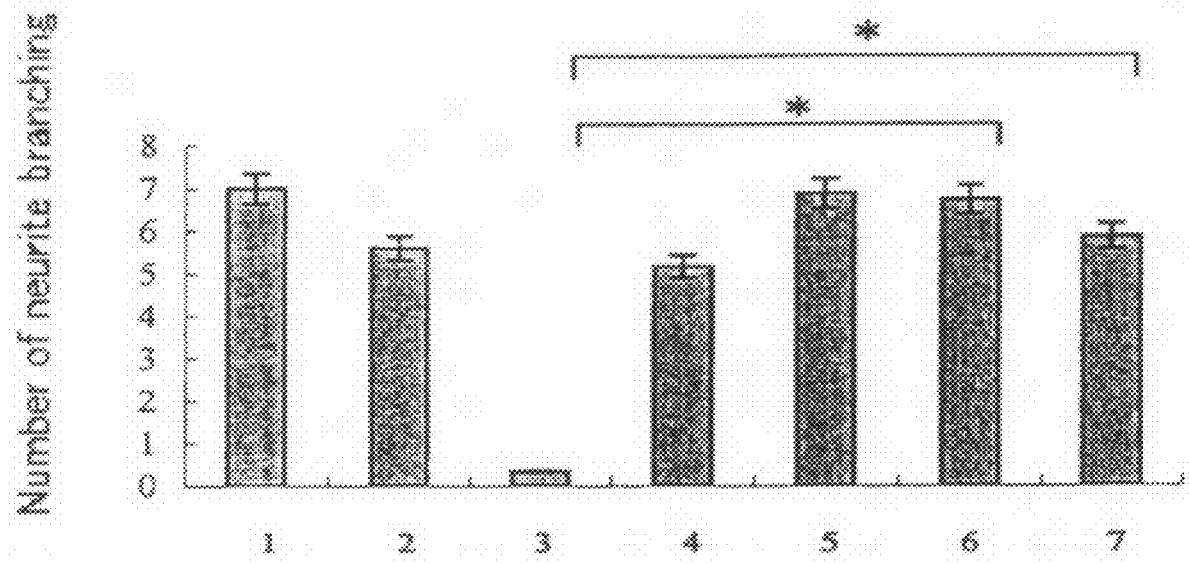

D.Melanogaster Eye Phenotype
AT x HMGB1

D.Melanogaster Eye Phenotype
Htt x HMGB1    Day 10 after birth

SEQUENCE LISTING

<160> NUMBER OF SEQ ID NOS: 12

<210> SEQ ID NO 1
<211> LENGTH: 648
<212> TYPE: DNA
<213> ORGANISM: Homo sapiens
<220> FEATURE:
<221> NAME/KEY: CDS
<222> LOCATION: (1)..(648)

<400> SEQUENCE: 1

```
atg ggc aaa gga gat cct aag aag ccg aga ggc aaa atg tca tca tat        48
Met Gly Lys Gly Asp Pro Lys Lys Pro Arg Gly Lys Met Ser Ser Tyr
 1               5                  10                  15 gca ttt ttt gtg caa act tgt cgg gag gag cat aag aag aag cac cca        96
Ala Phe Phe Val Gln Thr Cys Arg Glu Glu His Lys Lys Lys His Pro
             20                  25                  30 gat gct tca gtc aac ttc tca gag ttt tct aag aag tgc tca gag agg       144
Asp Ala Ser Val Asn Phe Ser Glu Phe Ser Lys Lys Cys Ser Glu Arg
         35                  40                  45 tgg aag acc atg tct gct aaa gag aaa gga aaa ttt gaa gat atg gca       192
Trp Lys Thr Met Ser Ala Lys Glu Lys Gly Lys Phe Glu Asp Met Ala
     50                  55                  60 aaa gcg gac aag gcc cgt tat gaa aga gaa atg aaa acc tat atc cct       240
Lys Ala Asp Lys Ala Arg Tyr Glu Arg Glu Met Lys Thr Tyr Ile Pro
 65                  70                  75                  80 ccc aaa ggg gag aca aaa aag aag ttc aag gat ccc aat gca ccc aag       288
Pro Lys Gly Glu Thr Lys Lys Lys Phe Lys Asp Pro Asn Ala Pro Lys
                 85                  90                  95 agg cct cct tcg gcc ttc ttc ctc ttc tgc tct gag tat cgc cca aaa       336
```

```
Arg Pro Pro Ser Ala Phe Phe Leu Phe Cys Ser Glu Tyr Arg Pro Lys
        100                 105                 110 atc aaa gga gaa cat cct ggc ctg tcc att ggt gat gtt gcg aag aaa       384
Ile Lys Gly Glu His Pro Gly Leu Ser Ile Gly Asp Val Ala Lys Lys
        115                 120                 125 ctg gga gag atg tgg aat aac act gct gca gat gac aag cag cct tat       432
Leu Gly Glu Met Trp Asn Asn Thr Ala Ala Asp Asp Lys Gln Pro Tyr
130                 135                 140 gaa aag aag gct gcg aag ctg aag gaa aaa tac gaa aag gat att gct       480
Glu Lys Lys Ala Ala Lys Leu Lys Glu Lys Tyr Glu Lys Asp Ile Ala
145                 150                 155                 160 gca tat cga gct aaa gga aag cct gat gca gca aaa aag gga gtt gtc       528
Ala Tyr Arg Ala Lys Gly Lys Pro Asp Ala Ala Lys Lys Gly Val Val
                165                 170                 175 aag gct gaa aaa agc aag aaa aag aag gaa gag gag gaa gat gag gaa       576
Lys Ala Glu Lys Ser Lys Lys Lys Glu Glu Glu Glu Asp Glu Glu
                180                 185                 190 gat gaa gag gat gag gag gag gaa gat gaa gaa gat gaa gat gaa           624
Asp Glu Glu Asp Glu Glu Glu Asp Glu Glu Asp Glu Asp Glu
                195                 200                 205 gaa gaa gat gat gat gat gat taa                                       648
Glu Glu Asp Asp Asp Asp Asp
        210                 215

<210> SEQ ID NO 2
<211> LENGTH: 215
<212> TYPE: PRT
<213> ORGANISM: Homo sapiens

<400> SEQUENCE: 2

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
                20                  25                  30

Asp Ala Ser Val Asn Phe Ser Glu Phe Ser Lys Lys Cys Ser Glu Arg
            35                  40                  45

Trp Lys Thr Met Ser Ala Lys Glu Lys Gly Lys Phe Glu Asp Met Ala
    50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Lys Phe Lys Asp Pro Asn Ala Pro Lys
                85                  90                  95

Arg Pro Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Asp Lys Gln Pro Tyr
130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Glu Glu Glu Glu Asp Glu Glu
            180                 185                 190

Asp Glu Glu Asp Glu Glu Glu Asp Glu Glu Asp Glu Asp Glu
        195                 200                 205

Glu Glu Asp Asp Asp Asp Asp
```

-continued

```
              210                 215

<210> SEQ ID NO 3
<211> LENGTH: 1109
<212> TYPE: DNA
<213> ORGANISM: Homo sapiens
<220> FEATURE:
<221> NAME/KEY: CDS
<222> LOCATION: (86)..(673)

<400> SEQUENCE: 3
cgtgagggaa gcgtctccgt tgggtccggc cgctctgcgg gactctgagg aaaagctcgc          60
accaggtgga cgcggatctg tcaac atg ggt aaa gga gac ccc aac aag ccg          112
                           Met Gly Lys Gly Asp Pro Asn Lys Pro
                             1               5 cgg ggc aaa atg tcc tcg tac gcc ttc ttc gtg cag acc tgc cgg gaa          160
Arg Gly Lys Met Ser Ser Tyr Ala Phe Phe Val Gln Thr Cys Arg Glu
 10              15                  20                  25 gag cac aag aag aaa cac ccg gac tct tcc gtc aat ttc gcg gaa ttc          208
Glu His Lys Lys Lys His Pro Asp Ser Ser Val Asn Phe Ala Glu Phe
             30                  35                  40 tcc aag aag tgt tcg gag aga tgg aag acc atg tct gca aag gag aag          256
Ser Lys Lys Cys Ser Glu Arg Trp Lys Thr Met Ser Ala Lys Glu Lys
         45                  50                  55 tcg aag ttt gaa gat atg gca aaa agt gac aaa gct cgc tat gac agg          304
Ser Lys Phe Glu Asp Met Ala Lys Ser Asp Lys Ala Arg Tyr Asp Arg
     60                  65                  70 gag atg aaa aat tac gtt cct ccc aaa ggt gat aag aag ggg aag aaa          352
Glu Met Lys Asn Tyr Val Pro Pro Lys Gly Asp Lys Lys Gly Lys Lys
 75                  80                  85 aag gac ccc aat gct cct aaa agg cca cca tct gcc ttc ttc ctg ttt          400
Lys Asp Pro Asn Ala Pro Lys Arg Pro Pro Ser Ala Phe Phe Leu Phe
 90                  95                 100                 105 tgc tct gaa cat cgc cca aag atc aaa agt gaa cac cct ggc cta tcc          448
Cys Ser Glu His Arg Pro Lys Ile Lys Ser Glu His Pro Gly Leu Ser
             110                 115                 120 att ggg gat act gca aag aaa ttg ggt gaa atg tgg tct gag cag tca          496
Ile Gly Asp Thr Ala Lys Lys Leu Gly Glu Met Trp Ser Glu Gln Ser
         125                 130                 135 gcc aaa gat aaa caa cca tat gaa cag aaa gca gct aag cta aag gag          544
Ala Lys Asp Lys Gln Pro Tyr Glu Gln Lys Ala Ala Lys Leu Lys Glu
     140                 145                 150 aaa tat gaa aag gat att gct gca tat cgt gcc aag ggc aaa agt gaa          592
Lys Tyr Glu Lys Asp Ile Ala Ala Tyr Arg Ala Lys Gly Lys Ser Glu
 155                 160                 165 gca gga aag aag ggc cct ggc agg cca aca ggc tca aag aag aag aac          640
Ala Gly Lys Lys Gly Pro Gly Arg Pro Thr Gly Ser Lys Lys Lys Asn
170                 175                 180                 185 gaa cca gaa gat gag gag gag gag gag gaa taa taagatgaag atgaggagga         693
Glu Pro Glu Asp Glu Glu Glu Glu Glu
                190                 195 agaggatgaa gatgaagaat aaatggctat cctttaatga tgcgtgtgga atgtgtgtgt         753
gtgctcaggc aattattttg ctaagaatgt gaattcaagt gcagctcaat actagcttca         813
gtataaaaac tgtacagatt tttgtatagc tgataagatt ctctgtagag aaaatacttt         873
taaaaaatgc aggttgtagc tttttgatgg gctactcata cagttagatt ttacagcttc         933
tgatgttgaa tgttcctaaa tatttaatgg tttttttaat ttcttgtgta tggtagcaca         993
gcaaacttgt aggaattagt atcaatagta aattttgggt ttttaggat gttgcatttc         1053
```

```
gttttttttaa aaaaaatttt gtaataaaat tatgtatatt aaaaaaaaaa aaaaaa      1109
```

<210> SEQ ID NO 4
<211> LENGTH: 195
<212> TYPE: PRT
<213> ORGANISM: Homo sapiens

<400> SEQUENCE: 4

```
Met Gly Lys Gly Asp Pro Asn Lys Pro Arg Gly Lys Met Ser Ser Tyr
 1               5                  10                  15

Ala Phe Phe Val Gln Thr Cys Arg Glu Glu His Lys Lys Lys His Pro
            20                  25                  30

Asp Ser Ser Val Asn Phe Ala Glu Phe Ser Lys Lys Cys Ser Glu Arg
        35                  40                  45

Trp Lys Thr Met Ser Ala Lys Glu Lys Ser Lys Phe Glu Asp Met Ala
 50                  55                  60

Lys Ser Asp Lys Ala Arg Tyr Asp Arg Glu Met Lys Asn Tyr Val Pro
 65                  70                  75                  80

Pro Lys Gly Asp Lys Lys Gly Lys Lys Asp Pro Asn Ala Pro Lys
                85                  90                  95

Arg Pro Pro Ser Ala Phe Phe Leu Phe Cys Ser Glu His Arg Pro Lys
                100                 105                 110

Ile Lys Ser Glu His Pro Gly Leu Ser Ile Gly Asp Thr Ala Lys Lys
                115                 120                 125

Leu Gly Glu Met Trp Ser Glu Gln Ser Ala Lys Asp Lys Gln Pro Tyr
130                 135                 140

Glu Gln Lys Ala Ala Lys Leu Lys Glu Lys Tyr Glu Lys Asp Ile Ala
145                 150                 155                 160

Ala Tyr Arg Ala Lys Gly Lys Ser Glu Ala Gly Lys Lys Gly Pro Gly
                165                 170                 175

Arg Pro Thr Gly Ser Lys Lys Lys Asn Glu Pro Glu Asp Glu Glu Glu
                180                 185                 190

Glu Glu Glu
        195
```

<210> SEQ ID NO 5
<211> LENGTH: 1117
<212> TYPE: DNA
<213> ORGANISM: Homo sapiens
<220> FEATURE:
<221> NAME/KEY: CDS
<222> LOCATION: (96)..(725)

<400> SEQUENCE: 5

```
ccgttgggtc cggccgctct gcgggactct gaggaaaagc tcgcaccagg caagaatacc       60
ctccaatacc ctcgggtgga cgcggatctg tcaac atg ggt aaa gga gac ccc        113
                                      Met Gly Lys Gly Asp Pro
                                       1               5 aac aag ccg cgg ggc aaa atg tcc tcg tac gcc ttc ttc gtg cag acc       161
Asn Lys Pro Arg Gly Lys Met Ser Ser Tyr Ala Phe Phe Val Gln Thr
            10                  15                  20 tgc cgg gaa gag cac aag aag aaa cac ccg gac tct tcc gtc aat ttc       209
Cys Arg Glu Glu His Lys Lys Lys His Pro Asp Ser Ser Val Asn Phe
 25                  30                  35 gcg gaa ttc tcc aag aag tgt tcg gag aga tgg aag acc atg tct gca       257
Ala Glu Phe Ser Lys Lys Cys Ser Glu Arg Trp Lys Thr Met Ser Ala
            40                  45                  50 aag gag aag tcg aag ttt gaa gat atg gca aaa agt gac aaa gct cgc       305
Lys Glu Lys Ser Lys Phe Glu Asp Met Ala Lys Ser Asp Lys Ala Arg
```

-continued

| | | |
|---|---|---|
| Lys Glu Lys Ser Lys Phe Glu Asp Met Ala Lys Ser Asp Lys Ala Arg<br>55                   60                   65                   70 | |
| tat gac agg gag atg aaa aat tac gtt cct ccc aaa ggt gat aag aag<br>Tyr Asp Arg Glu Met Lys Asn Tyr Val Pro Pro Lys Gly Asp Lys Lys<br>               75                   80                   85 | 353 |
| ggg aag aaa aag gac ccc aat gct cct aaa agg cca cca tct gcc ttc<br>Gly Lys Lys Lys Asp Pro Asn Ala Pro Lys Arg Pro Pro Ser Ala Phe<br>               90                   95                   100 | 401 |
| ttc ctg ttt tgc tct gaa cat cgc cca aag atc aaa agt gaa cac cct<br>Phe Leu Phe Cys Ser Glu His Arg Pro Lys Ile Lys Ser Glu His Pro<br>         105                   110                   115 | 449 |
| ggc cta tcc att ggg gat act gca aag aaa ttg ggt gaa atg tgg tct<br>Gly Leu Ser Ile Gly Asp Thr Ala Lys Lys Leu Gly Glu Met Trp Ser<br>         120                   125                   130 | 497 |
| gag cag tca gcc aaa gat aaa caa cca tat gaa cag aaa gca gct aag<br>Glu Gln Ser Ala Lys Asp Lys Gln Pro Tyr Glu Gln Lys Ala Ala Lys<br>135                   140                   145                   150 | 545 |
| cta aag gag aaa tat gaa aag gat att gct gca tat cgt gcc aag ggc<br>Leu Lys Glu Lys Tyr Glu Lys Asp Ile Ala Ala Tyr Arg Ala Lys Gly<br>                   155                   160                   165 | 593 |
| aaa agt gaa gca gga aag aag ggc cct ggc agg cca aca ggc tca aag<br>Lys Ser Glu Ala Gly Lys Lys Gly Pro Gly Arg Pro Thr Gly Ser Lys<br>         170                   175                   180 | 641 |
| aag aag aac gaa cca gaa gat gag gag gag gag gaa gaa gaa gat<br>Lys Lys Asn Glu Pro Glu Asp Glu Glu Glu Glu Glu Glu Glu Asp<br>               185                   190                   195 | 689 |
| gaa gat gag gag gaa gag gat gaa gat gaa gaa taa atggctatcc<br>Glu Asp Glu Glu Glu Glu Asp Glu Asp Glu Glu<br>200                   205                   210 | 735 |
| tttaatgatg cgtgtggaat gtgtgtgtgt gctcaggcaa ttattttgct aagaatgtga | 795 |
| attcaagtgc agctcaatac tagcttcagt ataaaaactg tacagatttt gtatagctga | 855 |
| taagattctc tgtagagaaa atactttttaa aaaatgcagg ttgtagcttt ttgatgggct | 915 |
| actcatacag ttagatttta cagcttctga tgttgaatgt tcctaaatat ttaatggttt | 975 |
| ttttaatttc ttgtgtatgg tagcacagca aacttgtagg aattagtatc aatagtaaat | 1035 |
| tttgggtttt ttaggatgtt gcatttcgtt tttttaaaaa aattttgta ataaaattat | 1095 |
| gtatattaaa aaaaaaaaaa aa | 1117 |

<210> SEQ ID NO 6
<211> LENGTH: 209
<212> TYPE: PRT
<213> ORGANISM: Homo sapiens

<400> SEQUENCE: 6

Met Gly Lys Gly Asp Pro Asn Lys Pro Arg Gly Lys Met Ser Ser Tyr
1                 5                   10                   15

Ala Phe Phe Val Gln Thr Cys Arg Glu Glu His Lys Lys Lys His Pro
                 20                   25                   30

Asp Ser Ser Val Asn Phe Ala Glu Phe Ser Lys Lys Cys Ser Glu Arg
           35                   40                   45

Trp Lys Thr Met Ser Ala Lys Glu Lys Ser Lys Phe Glu Asp Met Ala
   50                   55                   60

Lys Ser Asp Lys Ala Arg Tyr Asp Arg Glu Met Lys Asn Tyr Val Pro
65                   70                   75                   80

Pro Lys Gly Asp Lys Lys Gly Lys Lys Lys Asp Pro Asn Ala Pro Lys
                 85                   90                   95

```
Arg Pro Pro Ser Ala Phe Phe Leu Phe Cys Ser Glu His Arg Pro Lys
            100                 105                 110

Ile Lys Ser Glu His Pro Gly Leu Ser Ile Gly Asp Thr Ala Lys Lys
        115                 120                 125

Leu Gly Glu Met Trp Ser Glu Gln Ser Ala Lys Asp Lys Gln Pro Tyr
    130                 135                 140

Glu Gln Lys Ala Ala Lys Leu Lys Glu Lys Tyr Glu Lys Asp Ile Ala
145                 150                 155                 160

Ala Tyr Arg Ala Lys Gly Lys Ser Glu Ala Gly Lys Lys Gly Pro Gly
                165                 170                 175

Arg Pro Thr Gly Ser Lys Lys Lys Asn Glu Pro Glu Asp Glu Glu Glu
            180                 185                 190

Glu Glu Glu Glu Glu Asp Glu Asp Glu Glu Glu Asp Glu Asp Glu Glu
        195                 200                 205

Glu

<210> SEQ ID NO 7
<211> LENGTH: 827
<212> TYPE: DNA
<213> ORGANISM: Homo sapiens
<220> FEATURE:
<221> NAME/KEY: CDS
<222> LOCATION: (192)..(794)

<400> SEQUENCE: 7
cgcaccgccc gctcccgccg ccgccgccgc cgccgccgcc gccgccgcag cgcccgcaca    60
actttccggc ccgcgccgcc gtgagcgcgc cctgccgccg cctcccctg cctctactcc    120 ccattccctt cccgccccct ccgccttccc tcctgctagg cggccgggaa ggaagaagca    180
attcagtcag g atg gct aaa ggt gac ccc aag aaa cca aag ggc aag atg    230
            Met Ala Lys Gly Asp Pro Lys Lys Pro Lys Gly Lys Met
              1               5                  10 tcc gct tat gcc ttc ttt gtg cag aca tgc aga gaa gaa cat aag aag    278
Ser Ala Tyr Ala Phe Phe Val Gln Thr Cys Arg Glu Glu His Lys Lys
         15                  20                  25 aaa aac cca gag gtc cct gtc aat ttt gcg gaa ttt tcc aag aag tgc    326
Lys Asn Pro Glu Val Pro Val Asn Phe Ala Glu Phe Ser Lys Lys Cys
 30                  35                  40                  45 tct gag agg tgg aag acg atg tcc ggg aaa gag aaa tct aaa ttt gat    374
Ser Glu Arg Trp Lys Thr Met Ser Gly Lys Glu Lys Ser Lys Phe Asp
                 50                  55                  60 gaa atg gca aag gca gat aaa gtg cgc tat gat cgg gaa atg aag gat    422
Glu Met Ala Lys Ala Asp Lys Val Arg Tyr Asp Arg Glu Met Lys Asp
             65                  70                  75 tat gga cca gct aag gga ggc aag aag aag aag gat cct aat gct ccc    470
Tyr Gly Pro Ala Lys Gly Gly Lys Lys Lys Lys Asp Pro Asn Ala Pro
         80                  85                  90 aaa agg cca ccg tct gga ttc ttc ctg ttc tgt tca gaa ttc cgc ccc    518
Lys Arg Pro Pro Ser Gly Phe Phe Leu Phe Cys Ser Glu Phe Arg Pro
     95                 100                 105 aag atc aaa tcc aca aac ccc ggc atc tct att gga gac gtg gca aaa    566
Lys Ile Lys Ser Thr Asn Pro Gly Ile Ser Ile Gly Asp Val Ala Lys
110                 115                 120                 125 aag ctg ggt gag atg tgg aat aat tta aat gac agt gaa aag cag cct    614
Lys Leu Gly Glu Met Trp Asn Asn Leu Asn Asp Ser Glu Lys Gln Pro
                130                 135                 140 tac atc act aag gcg gca aag ctg aag gag aag tat gag aag gat gtt    662
Tyr Ile Thr Lys Ala Ala Lys Leu Lys Glu Lys Tyr Glu Lys Asp Val
            145                 150                 155
```

```
gct gac tat aag tcg aaa gga aag ttt gat ggt gca aag ggt cct gct      710
Ala Asp Tyr Lys Ser Lys Gly Lys Phe Asp Gly Ala Lys Gly Pro Ala
        160                 165                 170 aaa gtt gcc cgg aaa aag gtg gaa gag gaa gat gaa gaa gag gag          758
Lys Val Ala Arg Lys Lys Val Glu Glu Glu Asp Glu Glu Glu Glu
175                 180                 185 gaa gaa gag gag gag gag gag gag gag gat gaa taa agaaactgtt           804
Glu Glu Glu Glu Glu Glu Glu Glu Asp Glu
190                 195                 200 tatctgtcaa aaaaaaaaaa aaa                                            827

<210> SEQ ID NO 8
<211> LENGTH: 200
<212> TYPE: PRT
<213> ORGANISM: Homo sapiens

<400> SEQUENCE: 8

Met Ala Lys Gly Asp Pro Lys Lys Pro Lys Gly Lys Met Ser Ala Tyr
  1               5                  10                  15

Ala Phe Phe Val Gln Thr Cys Arg Glu Glu His Lys Lys Lys Asn Pro
                 20                  25                  30

Glu Val Pro Val Asn Phe Ala Glu Phe Ser Lys Lys Cys Ser Glu Arg
             35                  40                  45

Trp Lys Thr Met Ser Gly Lys Glu Ser Lys Phe Asp Glu Met Ala
 50                  55                  60

Lys Ala Asp Lys Val Arg Tyr Asp Arg Glu Met Lys Asp Tyr Gly Pro
 65                  70                  75                  80

Ala Lys Gly Gly Lys Lys Lys Asp Pro Asn Ala Pro Lys Arg Pro
                 85                  90                  95

Pro Ser Gly Phe Phe Leu Phe Cys Ser Glu Phe Arg Pro Lys Ile Lys
            100                 105                 110

Ser Thr Asn Pro Gly Ile Ser Ile Gly Asp Val Ala Lys Leu Gly
            115                 120                 125

Glu Met Trp Asn Asn Leu Asn Asp Ser Glu Lys Gln Pro Tyr Ile Thr
130                 135                 140

Lys Ala Ala Lys Leu Lys Glu Lys Tyr Glu Lys Asp Val Ala Asp Tyr
145                 150                 155                 160

Lys Ser Lys Gly Lys Phe Asp Gly Ala Lys Gly Pro Ala Lys Val Ala
                165                 170                 175

Arg Lys Lys Val Glu Glu Glu Asp Glu Glu Glu Glu Glu Glu Glu Glu
            180                 185                 190

Glu Glu Glu Glu Glu Glu Asp Glu
        195                 200

<210> SEQ ID NO 9
<211> LENGTH: 1361
<212> TYPE: DNA
<213> ORGANISM: Rattus norvegicus
<220> FEATURE:
<221> NAME/KEY: CDS
<222> LOCATION: (134)..(781)

<400> SEQUENCE: 9
gaggaggctg cgtctggctc ccgctctcac agccattgca gtacattgag ctccatagag     60
acagcgccgg ggcaagcgag agccggacgg gcactgggcg actctgtgcc tcgcggagga    120
aaatcaacta aac atg ggc aaa gga gat cct aag aag ccg aga ggc aaa       169
            Met Gly Lys Gly Asp Pro Lys Lys Pro Arg Gly Lys
```

```
                    1               5                   10
atg tcc tca tat gca ttc ttt gtg caa acc tgc cgg gag gag cac aag        217
Met Ser Ser Tyr Ala Phe Phe Val Gln Thr Cys Arg Glu Glu His Lys
            15                  20                  25 aag aag cac ccg gat gct tct gtc aac ttc tca gag ttc tcc aag aag        265
Lys Lys His Pro Asp Ala Ser Val Asn Phe Ser Glu Phe Ser Lys Lys
        30                  35                  40 tgc tca gag agg tgg aag acc atg tct gct aaa gaa aag ggg aaa ttt        313
Cys Ser Glu Arg Trp Lys Thr Met Ser Ala Lys Glu Lys Gly Lys Phe
45                  50                  55                  60 gaa gat atg gca aag gct gac aag gct cgt tat gaa aga gaa atg aaa        361
Glu Asp Met Ala Lys Ala Asp Lys Ala Arg Tyr Glu Arg Glu Met Lys
                65                  70                  75 acc tac atc ccc ccc aaa ggg gag acc aaa aag aag ttc aag gac ccc        409
Thr Tyr Ile Pro Pro Lys Gly Glu Thr Lys Lys Lys Phe Lys Asp Pro
            80                  85                  90 aat gcc ccc aag agg cct cct tcg gcc ttc ttc ttg ttc tgt tct gag        457
Asn Ala Pro Lys Arg Pro Pro Ser Ala Phe Phe Leu Phe Cys Ser Glu
        95                  100                 105 tac cgc cca aaa atc aaa ggc gag cat cct ggc tta tcc att ggt gat        505
Tyr Arg Pro Lys Ile Lys Gly Glu His Pro Gly Leu Ser Ile Gly Asp
110                 115                 120 gtt gcg aag aaa cta gga gag atg tgg aac aac act gct gcg gat gac        553
Val Ala Lys Lys Leu Gly Glu Met Trp Asn Asn Thr Ala Ala Asp Asp
125                 130                 135                 140 aag cag ccc tat gaa aag aag gcc gcc aag ctg aag gag aag tat gag        601
Lys Gln Pro Tyr Glu Lys Lys Ala Ala Lys Leu Lys Glu Lys Tyr Glu
                145                 150                 155 aag gat att gct gcc tac aga gct aaa gga aaa cct gat gca gcg aaa        649
Lys Asp Ile Ala Ala Tyr Arg Ala Lys Gly Lys Pro Asp Ala Ala Lys
            160                 165                 170 aag ggg gtg gtc aag gct gag aag agc aag aaa aag aag gaa gag gaa        697
Lys Gly Val Val Lys Ala Glu Lys Ser Lys Lys Lys Lys Glu Glu Glu
        175                 180                 185 gac gac gag gag gat gaa gag gat gag gaa gag gag gaa gag gag gaa        745
Asp Asp Glu Glu Asp Glu Glu Asp Glu Glu Glu Glu Glu Glu Glu Glu
190                 195                 200 gac gaa gat gaa gaa gaa gat gat gat gat gaa taa gttggttcta             791
Asp Glu Asp Glu Glu Glu Asp Asp Asp Asp Glu
205                 210                 215 gcgcagtttt ttttcttgt ctataaagca tttaaccccc ctgtacacaa ctcactcctt       851
ttaaagaaaa aaattgaaat gtaaggctgt gtaagatttg tttttaaact gtacagtgtc      911
tttttttgta tagttaacac actaccgaat gtgtctttag ctagccctgt cctggtggta      971
ttttcaatag ccactaacct tgcctggtac agtctggggg ttgtaaattg gcatggaaat      1031
taaagcaggt tcttgttggt gcacagcaca aattagttat atatggggac agtagtttgg     1091
tttttggttt cttttttttt tttttttttg gtttggtttt ttttcctttt gttttttttt      1151
tccatcttca gttgtctctg atgcagctta tacgaaggta attgttgttc tgttaactga      1211
ataccactct gtaattgcaa aaaaatggcg gctgttttgt tgacattctg aatgcttcta      1271
agtaaataca attttttta ttaaaaaaaa aaaaaaaaaa aaaaaaaaaa aaaaaaaaaa       1331
aaaaaaaaaa aaaaaaaaaa aaaaaaaaaa                                       1361

<210> SEQ ID NO 10
<211> LENGTH: 215
<212> TYPE: PRT
<213> ORGANISM: Rattus norvegicus
```

-continued

<400> SEQUENCE: 10

Met Gly Lys Gly Asp Pro Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ala Ser Val Asn Phe Ser Glu Phe Ser Lys Lys Cys Ser Glu Arg
        35                  40                  45

Trp Lys Thr Met Ser Ala Lys Glu Lys Gly Lys Phe Glu Asp Met Ala
    50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Lys Phe Lys Asp Pro Asn Ala Pro Lys
                85                  90                  95

Arg Pro Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Lys Gln Pro Tyr
    130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Glu Glu Glu Asp Glu Glu
            180                 185                 190

Asp Glu Glu Asp Glu Glu Glu Glu Glu Glu Asp Glu Asp
        195                 200                 205

Glu Glu Asp Asp Asp Asp Glu
    210                 215

<210> SEQ ID NO 11
<211> LENGTH: 1225
<212> TYPE: DNA
<213> ORGANISM: Rattus norvegicus
<220> FEATURE:
<221> NAME/KEY: CDS
<222> LOCATION: (153)..(785)

<400> SEQUENCE: 11
cgtcaagttg ccgtggcgcg gagaactctg caaaacaaga ggctggggat tgcgttagtg      60
ataagccagt tctcgccgga gcttggggaa ggaagtctct ctgtggaggt ctgagggaag    120
agctcgcgcc aggtagacgc tgcgccgtca tc atg ggc aag ggg gac ccc aac      173
                                   Met Gly Lys Gly Asp Pro Asn
                                   1               5 aag ccg cgg ggc aag atg tcc tcg tac gcc ttc ttc gtg cag acc tgc      221
Lys Pro Arg Gly Lys Met Ser Ser Tyr Ala Phe Phe Val Gln Thr Cys
            10                  15                  20 cgg gag gag cac aag aag aag cat ccc gac tcg tcg gtc aac ttc gcc      269
Arg Glu Glu His Lys Lys Lys His Pro Asp Ser Ser Val Asn Phe Ala
    25                  30                  35 gag ttc tcg aag aaa tgt tcg gag aga tgg aag acc atg tct gcc aag      317
Glu Phe Ser Lys Lys Cys Ser Glu Arg Trp Lys Thr Met Ser Ala Lys
40                  45                  50                  55 gaa aag tcg aag ttt gag gat ttg gcc aag agc gac aaa gct cgt tat      365
Glu Lys Ser Lys Phe Glu Asp Leu Ala Lys Ser Asp Lys Ala Arg Tyr
                60                  65                  70

-continued

```
gac agg gag atg aag aac tat gtt cct ccc aaa ggt gat aag aaa gga      413
Asp Arg Glu Met Lys Asn Tyr Val Pro Pro Lys Gly Asp Lys Lys Gly
            75                  80                  85 aag aaa aaa gat cca aat gct ccc aag aga cca ccg tct gcc ttc ttc      461
Lys Lys Lys Asp Pro Asn Ala Pro Lys Arg Pro Pro Ser Ala Phe Phe
        90                  95                 100 ctg ttt tgc tct gaa cat cgc cca aag atc aaa agt gaa cac ccc ggc      509
Leu Phe Cys Ser Glu His Arg Pro Lys Ile Lys Ser Glu His Pro Gly
    105                 110                 115 ctg tct att gga gat act gca aag aaa ctg ggg gag atg tgg tct gag      557
Leu Ser Ile Gly Asp Thr Ala Lys Lys Leu Gly Glu Met Trp Ser Glu
120                 125                 130                 135 caa tct gcc aaa gat aaa caa ccg tat gag cag aaa gca gct aaa cta      605
Gln Ser Ala Lys Asp Lys Gln Pro Tyr Glu Gln Lys Ala Ala Lys Leu
                140                 145                 150 aag gag aag tat gaa aag gat att gct gca tac cgt gcc aag ggc aaa      653
Lys Glu Lys Tyr Glu Lys Asp Ile Ala Ala Tyr Arg Ala Lys Gly Lys
            155                 160                 165 agt gaa gta gga aag aag ggt cct ggt agg cca aca ggc tca aag aag      701
Ser Glu Val Gly Lys Lys Gly Pro Gly Arg Pro Thr Gly Ser Lys Lys
        170                 175                 180 aag aat gaa cca gaa gat gag gaa gag gag gag gag gaa gat gat          749
Lys Asn Glu Pro Glu Asp Glu Glu Glu Glu Glu Glu Asp Asp
    185                 190                 195 gaa gat gaa gag gag gaa gat gag gat gaa gaa taa gtatctgtcc           795
Glu Asp Glu Glu Glu Glu Asp Glu Asp Glu Glu
200                 205                 210 taaagtgtgg agtatatgtg ctcaggcaat tattttgcta agaatgtgaa attcaagtgc    855
agctcaacat tagcttcagt ataaaaactg tacagatttt tgtatagctg atgagattct    915
ttgtagagaa aatactttt aaaaggggtt tgtagctttt tcaggggcta caacgtacag     975
ttagatttaa agcttttgat gttgaatgtt tctaaatatt taatggtttc tttaatttct   1035
tatgatagca aaaaaaaaac ttcataggaa tttgtattac cagtaaaaga attttttttt   1095
ttaggatgtt gcattttgt tttttttaaa tttgtaataa aataatgtat attacttgaa    1155
aaaaaaaaaa aaaaaaaaaa aaaaaaaaaa aaaaaaaaaa aaaaaaaaaa aaaaaaaaaa   1215
aaaaaaaaaa                                                         1225
```

<210> SEQ ID NO 12
<211> LENGTH: 210
<212> TYPE: PRT
<213> ORGANISM: Rattus norvegicus

<400> SEQUENCE: 12

```
Met Gly Lys Gly Asp Pro Asn Lys Pro Arg Gly Lys Met Ser Ser Tyr
 1               5                  10                  15

Ala Phe Phe Val Gln Thr Cys Arg Glu Glu His Lys Lys Lys His Pro
                20                  25                  30

Asp Ser Ser Val Asn Phe Ala Glu Phe Ser Lys Lys Cys Ser Glu Arg
            35                  40                  45

Trp Lys Thr Met Ser Ala Lys Glu Lys Ser Lys Phe Glu Asp Leu Ala
        50                  55                  60

Lys Ser Asp Lys Ala Arg Tyr Asp Arg Glu Met Lys Asn Tyr Val Pro
 65                  70                  75                  80

Pro Lys Gly Asp Lys Lys Gly Lys Lys Asp Pro Asn Ala Pro Lys
                85                  90                  95
```

```
                    -continued

Arg Pro Pro Ser Ala Phe Phe Leu Phe Cys Ser Glu His Arg Pro Lys
            100                 105                 110

Ile Lys Ser Glu His Pro Gly Leu Ser Ile Gly Asp Thr Ala Lys Lys
            115                 120                 125

Leu Gly Glu Met Trp Ser Glu Gln Ser Ala Lys Asp Lys Gln Pro Tyr
    130                 135                 140

Glu Gln Lys Ala Ala Lys Leu Lys Glu Lys Tyr Glu Lys Asp Ile Ala
145                 150                 155                 160

Ala Tyr Arg Ala Lys Gly Lys Ser Glu Val Gly Lys Lys Gly Pro Gly
                165                 170                 175

Arg Pro Thr Gly Ser Lys Lys Lys Asn Glu Pro Glu Asp Glu Glu Glu
            180                 185                 190

Glu Glu Glu Glu Glu Asp Asp Glu Asp Glu Glu Glu Glu Asp Glu Asp
            195                 200                 205

Glu Glu
    210
```

PROPHYLACTIC/THERAPEUTIC AGENT FOR NEURODEGENERATIVE DISEASE

CROSS-REFERENCE TO RELATED APPLICATIONS

This is a continuation of Application No. PCT/JP2007/058873 filed on Apr. 24, 2007.

This application incorporates by reference the material contained on the compact disc submitted herewith. The disc contains the file entitled SEQUENCE LISTING 27231-10-N-MD003-08P-US, which was, created on Nov. 20, 2008.

BACKGROUND OF THE INVENTION

1. Field of the Invention

The present invention relates to a prophylactic/therapeutic agent for neurodegenerative diseases (such as polyglutamine diseases), as well as to a method for screening substances that are effective in the prevention/treatment of neurodegenerative diseases (such as polyglutamine diseases).

2. Description of the Related Art

Polyglutamine diseases, including Huntington's disease, are neurodegenerative diseases caused by an abnormally expanded polyglutamine tract in the causative gene products. To date, few substances have been reported to be effective in the prevention/treatment of polyglutamine diseases although there are some reports that suggest the effectiveness of creatine, a compound involved in muscle contraction, and minocycline, an apoptosis inhibitor, in a Huntington's disease mouse model. While it is widely suggested that apoptotic cell death occurs in the cell model of polyglutamine diseases, the actual clinical use of apoptosis inhibitors is associated with considerable difficulty.

Under such circumstances, much attention has been drawn to the fact that the abnormal polyglutamine expansion induces the formation of insoluble protein aggregates within the nuclei and, thus, the use of inhibitors of polyglutamine-induced protein aggregation in the prevention or treatment of polyglutamine diseases has been proposed. For example, Japanese Patent Application Laid-Open (JP-A) No. 2003-267874 discloses specific oligosaccharides, or compounds having an oligosaccharide moiety, that inhibit the protein aggregation induced by an abnormal polyglutamine expansion and can therefore be used in the prevention or treatment of polyglutamine diseases. Since the deposition of protein aggregates within neurons is a phenomenon observed not only in polyglutamine diseases, but also in Alzheimer's disease and other neurodegenerative diseases, inhibition of the protein aggregation within neurons is expected to provide a way to prevent or treat various neurodegenerative diseases.

HMGB protein family is a family of high mobility group (HMG) proteins. HMG proteins are a group of non-histone proteins that are extracted from chromatin with 0.35M NaCl and show a high mobility in electrophoresis. These proteins are present in the nuclei of all higher organisms and have highly conserved amino acid sequences among higher organisms. The proteins of HMGB family are abundant in the nuclei and are well conserved among different species, suggesting an important role of the HMGB family proteins in the nuclei. While the exact functions of HMGB family are still unknown, these proteins have two HMG boxes for DNA binding and have been reported to interact with transcription factors, site-specific recombinant proteins, DNA repair proteins, silencing complexes and viral proteins (see Agresti, A. et al., Curr. Opin. Genet Develop. 13, 170-178. (2003)) and have an acidic C-terminal domain rich in basic amino acids. It has also been reported that the HMGB proteins play a key role in the genomic DNA remodeling by being inserted between DNA and histone complexes (see Agresti, A. et al., Curr. Opin. Genet Develop. 13, 170-178. (2003), and Travers A. E. EMBO reports 4, 131-136. (2003)) and that these proteins facilitate nucleosome remodeling by binding preferentially to distorted DNA, bending DNA, loosening wrapped DNA and thus enhancing accessibility to chromatin-remodeling complexes (see Travers A. E. EMBO reports 4, 131-136. (2003)).

BRIEF SUMMARY OF THE INVENTION

Accordingly, it is an objective of the present invention to provide a prophylactic/therapeutic agent for neurodegenerative diseases (such as polyglutamine diseases).

It is another objective of the present invention to provide a method for screening substances that are effective in the prevention/treatment of neurodegenerative diseases (such as polyglutamine diseases).

The present invention has been completed based on the following novel findings:

HMGB family proteins bind to abnormal polyglutamine proteins produced in patients with a polyglutamine disease or other neurodegenerative diseases and become incorporated into the nuclear inclusion bodies, resulting in a decrease in the amount of the functional HMGB family proteins in the nuclei and, thus, the onset of polyglutamine diseases and other neurodegenerative diseases; and therefore, compensating for the loss of functional HMGB family proteins in the nucleus (for example, by replenishing the depleted HMGB family proteins), or preventing the decrease in these proteins (for example, by inhibiting the binding of HMGB family proteins to abnormal polyglutamine proteins) can lead to prevention/treatment of polyglutamine diseases and other neurodegenerative diseases. To achieve the foregoing objectives, the present invention provides prophylactic/therapeutic agents for neurodegenerative diseases, as well as methods for screening substances effective in the prevention/treatment of neurodegenerative diseases, as presented below:

(1) a prophylactic/therapeutic agent for neurodegenerative disease, the agent containing an HMGB family protein or a derivative thereof, (2) the prophylactic/therapeutic agent according to (1) above, wherein the HMGB family protein is a protein according to any one of (a) and (b) below:

(a) a protein having the amino acid sequence of SEQ ID NO: 2, 4, 6 or 8; and (b) a protein having an amino acid sequence resulting from deletion, substitution, addition or insertion of one or more amino acids in the amino acid sequence of SEQ ID NO: 2, 4, 6 or 8 and having binding activity to an abnormal polyglutamine protein produced in a neurodegenerative disease;

(3) the prophylactic/therapeutic agent according to (2) above, wherein the protein of (b) has at least one activity selected from the group consisting of transcription-enhancing activity, DNA-repair-enhancing activity and cell death-suppressing activity;

(4) a prophylactic/therapeutic agent for neurodegenerative disease, the agent containing a recombinant vector that can express an HMGB family protein or a derivative thereof, (5) the prophylactic/therapeutic agent according to (4) above, wherein the recombinant vector includes DNA according to any one of (c) to (f) below:

(c) DNA encoding a protein having an amino acid sequence of SEQ ID NO: 2, 4, 6 or 8;

(d) DNA encoding a protein that has an amino acid sequence resulting from deletion, substitution, addition or insertion of one or more amino acids in the amino acid sequence of SEQ ID NO: 2, 4, 6 or 8 and that has binding activity to an abnormal polyglutamine protein produced in a neurodegenerative disease;

(e) DNA having the base sequence of SEQ ID NO: 1, 3, 5 or 7; and (f) DNA that can hybridize with DNA complementary to the DNA having the base sequence of SEQ ID NO: 1, 3, 5 or 7 under stringent conditions and that encodes a protein having binding activity to an abnormal polyglutamine protein produced in a neurodegenerative disease.

(6) the prophylactic/therapeutic agent according to (5) above, wherein the protein encoded by the DNA according to any one of (d) and (f) has at least one activity selected from the group consisting of transcription-enhancing activity, DNA-repair-enhancing activity and cell death-suppressing activity;

(7) a method for screening a substance effective in the prevention/treatment of a neurodegenerative disease, the method including:

determining whether a test substance inhibits binding of an HMGB family protein or a derivative thereof to an abnormal polyglutamine protein produced in a neurodegenerative disease; and identifying the test substance to be effective in the prevention/treatment of the neurodegenerative disease if the test substance has inhibited the binding; and (8) a method for screening a substance effective in the prevention/treatment of a neurodegenerative disease, the method including:

determining whether a test substance induces expression of a gene encoding an HMGB family protein or a derivative thereof, and identifying the test substance to be effective in the prevention/treatment of the neurodegenerative disease if the test substance has induced the expression.

According to the present invention, there is provided a prophylactic/therapeutic agent for neurodegenerative diseases, such as polyglutamine diseases, as well as a method for screening substances effective in the prevention/treatment of neurodegenerative diseases, such as polyglutamine diseases.

BRIEF DESCRIPTION OF THE SEVERAL VIEWS OF THE DRAWINGS

FIG. 2A shows typical spots that differ significantly in signal intensity (twice or more) between soluble proteins prepared from nuclear extracts of neurons expressing normal polyglutamine proteins.

FIG. 2B shows typical spots that differ significantly in signal intensity (twice or more) between soluble proteins prepared from nuclear extracts of neurons expressing mutant polyglutamine proteins.

FIG. 3A shows the results of immunohistochemistry of HMGB1-expressing adenoviral vector-infected primary cortical neurons using anti-HMGB protein antibodies and anti-Htt (N18) or anti-AT1 (H21) antibodies (3 days after infection).

FIG. 3B shows the results of immunohistochemistry of HMGB2-expressing adenoviral vector-infected primary cortical neurons using anti-HMGB protein antibodies and anti-Htt (N18) or anti-AT1 (H21) antibodies (3 days after infection).

FIG. 7A shows the results of immunohistochemistry of HMGB1 and HMGB2 in wild-type and AT1 knock-in mice, along with the results of quantitative analysis of signal intensity.

FIG. 7B shows the results of quantitative analysis of HMGB1 signal intensity in FIG. 7A.

FIG. 7C shows the results of quantitative analysis of HMGB2 signal intensity in FIG. 7A.

FIG. 10C shows the results of quantitative analysis of the neurite branching of Purkinje cells.

DETAILED DESCRIPTION OF THE INVENTION

Figure 1:
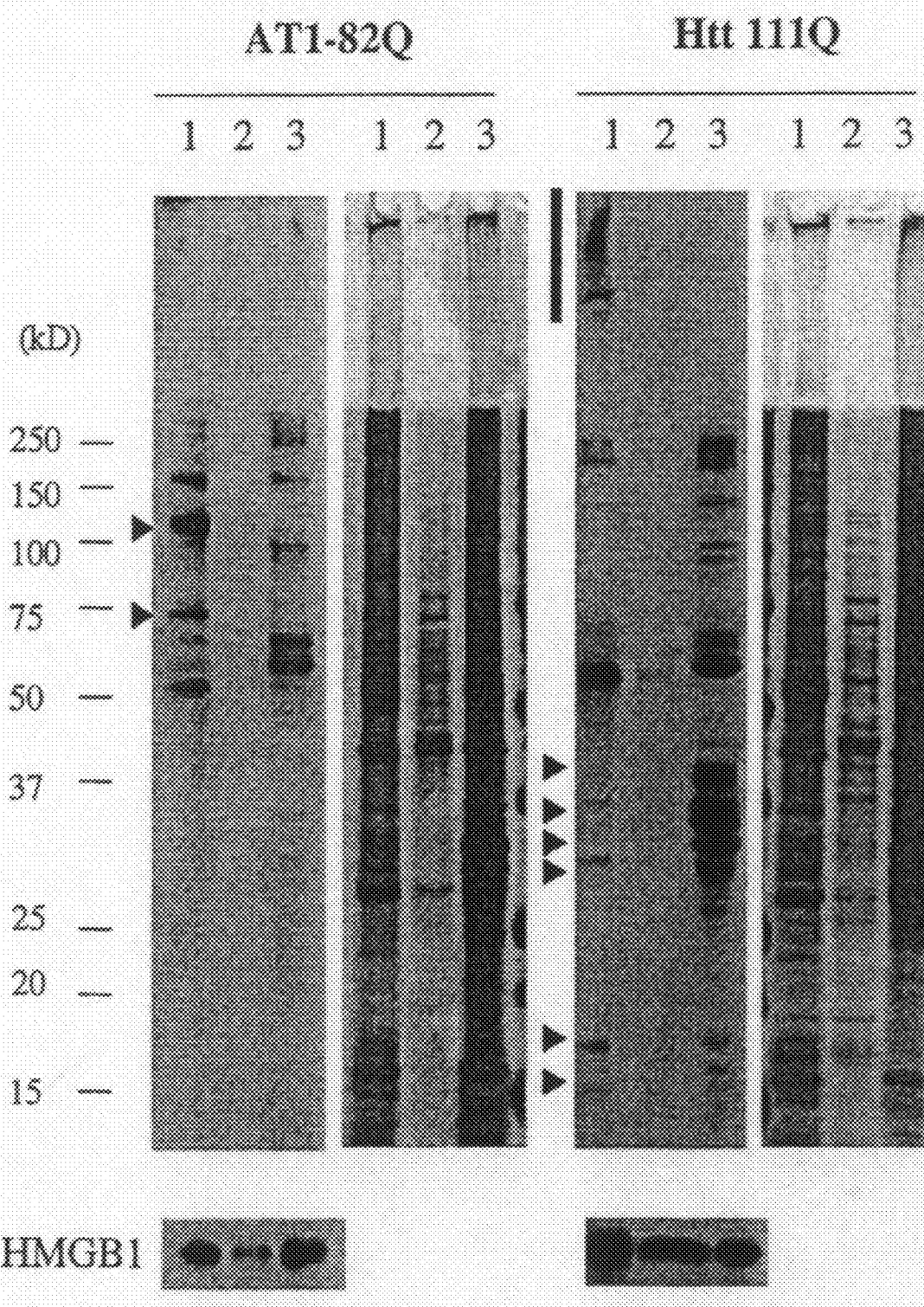
FIG. 1 shows the results of Western blot analysis using CAG53b antibody performed on whole cell lysates (Lanes 1) of cortical neurons expressing AT1-82Q or Htt111Q, each a mutant polyglutamine protein, as well as the results for soluble protein fractions (Lanes 2) and insoluble fractions (Lanes 3) of the nuclear extracts prepared from the same cells.

The present invention will now be described in details.

A prophylactic/therapeutic agent for neurodegenerative diseases according to the present invention contains an HMGB family protein or a derivative thereof, or a recombinant vector capable of expressing an HMGB family protein or a derivative thereof.

The term "HMGB family protein" includes any protein of HMGB family. Examples of the proteins of HMGB family include HMGB1, HMGB2 and HMGB3. The proteins of HMGB family share some common characteristics and functions: they are non-histone proteins that can be extracted from chromatin with 0.35M NaCl and show high mobility in electrophoresis; they are made up of about 200 amino acids and have HMG box as a common motif, they recognize DNA structures flexibly through their HMG boxes and bind to DNA in a non-sequence specific manner; they regulate transcription by bending DNA molecules; they interact with linker DNA between nucleosomes and affect chromatin remodeling; and they interact with transcription factors, site-specific recombinant enzymes, DNA repair proteins, viral proteins and many other molecules (Agresti, A. & amp; Bianchi, M. E. (2003) HMGB proteins and gene expression. Curr. Opin. Genet Develop. 13 170-178).

The term "HMGB family protein" includes HMGB family proteins of any higher organism. Since the amino acid sequences of HMGB family proteins are highly conserved among higher organisms, a neurodegenerative disease in a particular biological species may be prevented or treated not only by an HMGB protein derived from the same species, but also by one derived from different species. For example, to prevent/treat neurodegenerative diseases in humans, HMGB family proteins derived from higher organisms other than humans may be used, as may the HMGB family proteins of human origin. However, it is preferred to use HMGB family proteins of human origin to prevent/treat neurodegenerative diseases in humans.

The term "HMGB family protein" includes, in addition to wild-type HMGB family proteins, mutant HMGB family proteins that retain binding activity to abnormal polyglutamine proteins produced in neurodegenerative diseases. A mutant HMGB family protein has an amino acid sequence that results from deletion, substitution, addition or insertion of one or more amino acids in the amino acid sequence of a corresponding wild-type HMGB family protein. The number and position of amino acids deleted, substituted, added or inserted in the wild-type HMGB family protein are not limited as long as the resulting mutants retain binding activity to abnormal polyglutamine proteins produced in neurodegenerative diseases. The number of amino acids deleted, substituted, added or inserted is typically in the range of 20 or less, and preferably in the range of 10 or less (for example, 5 or less, 3 or less or 1).

The mutant HMGB family protein preferably retains, in addition to the binding activity to abnormal polyglutamine proteins produced in neurodegenerative diseases, at least one of other activities, including transcription-enhancing activity, DNA-repair-enhancing activity and cell death-suppressing activity. The mutant HMGB family protein that retains binding activity to abnormal polyglutamine proteins produced in neurodegenerative diseases can bind to an abnormal polyglutamine protein to prevent an endogenous HMGB family protein from binding to the abnormal polyglutamine protein to become incorporated into the inclusion bodies. As a result, the decrease in the amount of functional endogenous HMGB family proteins in the nucleus is minimized, leading to prevention/treatment of neurodegenerative diseases. Wild-type HMGB family proteins can prevent/treat neurodegenerative diseases not only by acting by the same mechanism as the mutant HMGB family protein, but also by replacing the endogenous HMGB family protein that has been incorporated into the inclusion bodies. If the mutant HMGB family protein retains, not just the binding activity to abnormal polyglutamine proteins produced in neurodegenerative diseases, but transcription-enhancing activity, DNA-repair-enhancing activity, cell death-suppressing activity and other activities, it can treat/prevent neurodegenerative diseases by replacing the endogenous HMGB family protein that has been incorporated into the inclusion bodies.

Examples of the HMGB family protein include proteins according to any one of (a) and (b) below:

(a) a protein having the amino acid sequence of SEQ ID NO: 2, 4, 6 or 8 (referred to as protein (a), hereinafter);

(b) a protein having an amino acid sequence resulting from deletion, substitution, addition or insertion of one or more amino acids in the amino acid sequence of SEQ ID NO: 2, 4, 6 or 8 and having binding activity to an abnormal polyglutamine protein produced in neurodegenerative diseases (referred to as protein (b), hereinafter).

The protein having the amino acid sequence of SEQ ID NO: 2 is human HMGB1. The protein having the amino acid sequence of SEQ ID NO: 4 or 6 is human HMGB2. The protein having the amino acid sequence of SEQ ID NO: 8 is human HMGB3. The protein having the amino acid sequence of SEQ ID NO: 4 or 6 is a splicing variant.

The number and position of amino acids deleted, substituted, added or inserted in the amino acid sequence of SEQ ID NO: 2, 4, 6 or 8 are not limited as long as the resulting protein retains binding activity to abnormal polyglutamine proteins produced in neurodegenerative diseases. The number of amino acids deleted, substituted, added or inserted is typically in the range of 20 or less, and preferably in the range of 10 or less (for example, 5 or less, 3 or less or 1).

The protein (b) includes proteins resulting from artificially introducing a mutation such as deletion, substitution and addition into the protein (a), as well as naturally occurring proteins having a naturally occurring mutation such as deletion, substitution and addition introduced therein, or such proteins having a mutation such as deletion, substitution and addition artificially introduced therein. Examples of naturally occurring proteins having a mutation such as deletion, substitution and addition introduced therein include proteins derived from humans and other mammals (such as humans, monkeys, cows, sheep, goats, horses, pigs, rabbits, dogs, cats, mice and rats) (including proteins resulting from polymorphisms in genes of these mammals).

The term "abnormal polyglutamine protein produced in a neurodegenerative disease" refers to a protein containing an abnormally expanded polyglutamine tract that is produced by a causative gene of a neurodegenerative disease containing triplet (CAG) repeats encoding the polyglutamine tract. Examples of neurodegenerative diseases and their causative genes include Huntington's disease/huntingtin gene, spinocerebellar degeneration/ataxin-1, -2, -3, -6, -7, -17 genes, dentatorubral-pallidoluysian atrophy/DRPLA gene, and spinobulbar muscular atrophy/androgen receptor gene. An abnormally expanded polyglutamine tract present in abnormal polyglutamine proteins typically contains 40 or more glutamine residues.

The term "derivative of HMGB family protein" refers to any derivative that retains binding activity to an abnormal polyglutamine protein produced in a neurodegenerative disease. Examples of the derivatives of HMGB family protein include HMGB family proteins with added sugar chains, pharmaceutically acceptable salts of HMGB family proteins, and fused proteins containing HMGB family proteins.

While the type and position of sugar chain added to HMGB family proteins may vary depending on the type of host cells used to produce a desired HMGB family protein, proteins produced by any of such host cells are also included in the derivatives of HMGB family protein.

Examples of the pharmaceutically acceptable salts of HMGB family protein include non-toxic alkali metal salts, alkaline earth metal salts, ammonium salts and non-toxic acid addition salts, such as those formed with sodium, potassium, lithium, calcium, magnesium, barium and ammonium. Examples of the non-toxic acid addition salts include chlorinated salts, hydrochloric acid salts, hydrobromides, sulfates, bisulfates, acetates, oxalates, valerates, oleates, laurates, borates, benzoates, lactates, phosphates, p-toluenesulfonates (tosylates), citrates, maleates, fumarates, succinates, tartrates, sulfonates, glycolates, ascorbates and benzenesulfonates.

Examples of the proteins that can be fused with HMGB family protein include β-galactosidase, protein A, IgG-binding domain of protein A, chloramphenicol acetyltransferase, poly(Arg), poly(Glu), protein G, maltose-binding protein, glutathione S-transferase (GST), polyhistidine chain (His-tag), S-peptide, DNA-binding protein domain, Tac antigen, thioredoxin, green fluorescent protein, hemagglutinin protein (HA)-tag, FLAG-tag, Myc-tag, GAL4-AD, T7 gene 10 protein, bovine papilloma virus L1 protein, streptavidin, VSV-G-tag, TAT (trans-activating protein), and TAT-derived PTD (protein transduction domain). For example, an HMGB family protein may be fused with hemagglutinin protein (HA)-tag, FLAG-tag or GAL4-AD to improve the stability of the HMGB family protein within cells. An HMGB family protein may also be fused with TAT (trans-activating protein) or TAT-derived PTD (protein transduction domain) to allow the HMGB family protein to cross the cell membrane.

The term "recombinant vector that can express an HMGB family protein or a derivative thereof" refers to a recombinant vector that incorporates DNA encoding an HMGB family protein or a fusion protein containing an HMGB family protein and an upstream promoter. Such a recombinant vector can be constructed by inserting a DNA fragment encoding an HMGB family protein, or a fusion protein containing an HMGB family protein, into a suitable expression vector downstream from its promoter. It is necessary that the DNA fragment encoding an HMGB family protein or a fusion protein containing an HMGB family protein is integrated in the expression vector so that the DNA fragment is functional. To this end, the expression vector may contain, in addition to a promoter, a cis-element, such as an enhancer, a splicing signal, a poly (A) addition signal, a selection marker (such as dihydrofolate reductase gene, ampicillin resistance gene and neomycin resistance gene), a ribosome binding sequence (such as S-D sequence) and other regulatory sequences.

The expression vector may be any expression vector that can self-replicate within the cells of a subject with a neurodegenerative disease that needs to be prevented/treated, including a plasmid vector, a phage vector and a viral vector. Examples of the plasmid vector include plasmids derived from *E. coli* (such as pRSET, pBR322, pBR325, pUC118, pUC119, pUC18 and pUC19), plasmids derived from *Bacillus subtilis* (such as pUB110 and pTP5) and plasmids derived from yeast (such as YEp13, YEp24 and YCp50). Examples of the phage vector include λ phage (such as Charon4A, Charon21A, EMBL3, EMBL4, λgt10, λgt11, λZAP). Examples of the viral vector include animal viruses, such as retroviruses, vaccinia viruses and adenoviruses, and insect viruses, such as vaculoviruses.

The DNA encoding an HMGB family protein may be DNA according to (c) to (f) below:

(c) DNA encoding a protein having the amino acid sequence of SEQ ID NO: 2, 4, 6 or 8 (referred to as DNA (c), hereinafter);

(d) DNA encoding a protein having an amino acid sequence resulting from deletion, substitution, addition or insertion of one or more amino acids in the amino acid sequence of SEQ ID NO: 2, 4, 6 or 8 and having binding activity to an abnormal polyglutamine protein produced in a neurodegenerative disease (referred to as DNA (d), hereinafter);

(e) DNA having the base sequence of SEQ ID NO: 1, 3, 5 or 7 (referred to as DNA (e), hereinafter); and (f) DNA that can hybridize with DNA complementary to the DNA having the base sequence of SEQ ID NO: 1, 3, 5 or 7 under stringent conditions and that encodes a protein having binding activity to an abnormal polyglutamine protein produced in a neurodegenerative disease (referred to as DNA (f), hereinafter).

The DNA having the base sequence of SEQ ID NO: 1, 3, 5 or 7 encodes a protein having the amino acid sequence of SEQ ID NO: 2, 4, 6 or 8, respectively.

A typical example of what is meant by the term "stringent condition" is 42° C., 2×SSC and 0.1% SDS. A preferred condition is 65° C., 0.1×SSC and 0.1% SDS. The DNA that can hybridize with DNA complementary to the DNA having the base sequence of SEQ ID NO: 1, 3, 5 or 7 under stringent conditions includes DNA that has a 80% or higher, preferably a 95% or higher (for example, 97% or higher, 98% or higher, or 99% or higher) similarity to the DNA having the base sequence of SEQ ID NO: 1, 3, 5 or 7.

In addition to DNA obtained by artificially introducing mutations into DNA (c) or (e), the DNA (d) and (f) include naturally occurring DNA having a naturally occurring mutation introduced therein, as well as such DNA having a mutation artificially introduced therein. Examples of the naturally occurring DNA having a naturally occurring mutation introduced therein include those derived from humans and other mammals (such as humans, monkeys, cows, sheep, goats, horses, pigs, rabbits, dogs, cats, mice and rats) (including DNA resulting from polymorphisms in genes of these mammals). A mutation may be artificially introduced into the DNA (c) or (e) by using techniques such as site-specific mutagenesis. This can be done by using, for example, Mutant-K (TaKaRa), Mutant-G (TaKaRa) or LA-PCR in vitro Mutagenesis series kit (TaKaRa).

The DNA encoding an HMGB family protein can be obtained by constructing a cDNA library from mRNA extracted from tissue (such as brain, liver and kidney) of human or other mammals, and screening the cDNA library for clones containing the desired DNA with a probe synthesized based on the base sequence of SEQ ID NO: 1, 3, 5 or 7. Alternatively, the DNA encoding a desired HMGB family protein may be chemically synthesized when the base sequence of the protein is known. A commercially available DNA synthesizer, such as a DNA synthesizer based on the thiophosphite method (Shimadzu) or a DNA synthesizer based on the phosphoamidite method (Perkin Elmer), may be used to chemically synthesize the DNA.

The cDNA library may be constructed in the following manner: total RNA is obtained from tissue (such as brain, liver and kidney) of human or other mammals. Poly(A)+RNA (mRNA) is then isolated from the total RNA by techniques such as affinity column chromatography and batch process using oligo dT-cellulose and poly U-sepharose. Poly(A)+ RNA (mRNA) may also be isolated by sucrose density gradient centrifugation. Using an oligo dT primer and reverse transcriptase, the isolated mRNA is used as a template to synthesize a single-stranded cDNA, which in turn is used to synthesize a double-stranded cDNA. The resulting double-stranded cDNA is inserted into a suitable cloning vector to construct a recombinant vector. The recombinant vector is used to transform *E. coli* and other host cells and successful transformants are then selected by tetracycline resistance and ampicillin resistance. This completes the cDNA library. The cloning vector to construct the cDNA library may be any suitable vector that can self-replicate within the host cells, including phage vectors and plasmid vectors. The host cell may be *Escherichia coli* (*E. coli*) or other suitable cells. Transformation of *E. coli* or other host cells may be carried out, for example, by incubating competent cells prepared in the presence of calcium chloride, magnesium chloride or rubidium chloride with the recombinant vector. When a plasmid is used as the vector, it preferably contains drug-resistance genes such as tetracycline-resistance gene and ampicillin resistance gene.

A commercially available kit, such as SuperScript Plasmid System for cDNA Synthesis and Plasmid Cloning (Gibco BRL) and ZAP-cDNA Synthesis Kit (Stratagene), may be used to construct the cDNA library.

To screen the cDNA library for clones containing desired DNA, a primer synthesized based on the base sequence of SEQ ID NO: 1 or 3 is used in a polymerase chain reaction (PCR) to obtain PCR-amplified fragments. The PCR-amplified fragments may be subcloned into a suitable plasmid vector.

The desired DNA can then be obtained by screening the cDNA library by colony hybridization or plaque hybridization using the PCR-amplified fragments as a probe. The probe may be the PCR-amplified fragment labeled with a suitable label, such as an isotope (such as $^{32}P$ and $^{35}S$), biotin or digoxigenin. Clones containing the desired DNA may also be obtained by immunoscreening and other expression screening techniques using antibodies.

The DNA base sequence thus obtained can be inserted into a vector by a known technique either directly or after digestion with a restriction enzyme, and sequenced by a commonly used technique for base sequence analysis, such as the Maxam and Gilbert's chemical modification method and the dideoxynucleotide chain termination method. Alternatively, a sequencer, such as 373A DNA sequencer (Perkin Elmer), may be used to determine the sequence.

The DNA encoding an HMGB family protein obtained in the above-described manner can be expressed in host cells to produce the HMGB family protein, according to the following procedure.

[Construction of Recombinant Vector and Transformant]

To construct a recombinant vector, a properly sized DNA fragment containing the coding region of a desired protein is prepared. Some of the bases in the base sequence of the coding region of the desired protein may be substituted to provide optimum codons for expression in the host cells.

This DNA fragment is inserted into a suitable expression vector downstream from its promoter to construct a recombinant vector. The recombinant vector is then introduced into a suitable host cell to obtain a transformant capable of producing the desired protein. It is necessary that the DNA fragment is integrated in the vector so that the DNA fragment is functional. To this end, the vector may contain, in addition to a promoter, a cis-element, such as an enhancer, a splicing signal, a poly (A) addition signal, a selection marker (such as dihydrofolate reductase gene, ampicillin resistance gene and neomycin resistance gene), a ribosome binding sequence (S-D sequence) and other regulatory sequences.

The expression vector may be any expression vector that can self-replicate within host cells, including a plasmid vector, a phage vector and a viral vector. Examples of the plasmid vector include plasmids derived from *E. coli* (such as pRSET, pBR322, pBR325, pUC118, pUC119, pUC18 and pUC19), plasmids derived from *Bacillus subtilis* (such as pUB110 and pTP5) and plasmids derived from yeast (such as YEp13, YEp24 and YCp50). Examples of the phage vector include λ phage (such as Charon4A, Charon21A, EMBL3, EMBL4, λgt10, λgt11, λZAP). Examples of the viral vector include animal viruses, such as retroviruses, vaccinia viruses and adenoviruses, and insect viruses, such as vaculoviruses.

The host cell may be any type of cells that can express the desired gene, including prokaryotic cells, yeast, animal cells, insect cells and plant cells. Alternatively, living specimens of animals, plants, or silkworm may be used as hosts.

When the host cell is a bacterium, bacteria belonging to the genus *Escherichia*, such as *Escherichia coli*, the genus *Bacillus*, such as *Bacillus subtilis*, the genus *Pseudomonas*, such as *Pseudomonas putida*, or the genus *Rhizobium*, such as *Rhizobium meliloti*, may be used as the host cell. Specific examples of bacterial strains that can be used as the host cell include *Escherichia coli* strains such as *Escherichia coli* XL1-Blue, *Escherichia coli* XL2-Blue, *Escherichia coli* DH1, *Escherichia coli* K12, *Escherichia coli* JM109 and *Escherichia coli* HB101, and *Bacillus subtilis* strains such as *Bacillus subtilis* MI 114 and *Bacillus subtilis* 207-21. The promoter for use in the bacterial hosts may be any promoter that can promote the expression of the desired protein in *E. coli* and other bacteria, including trp promoter, lac promoter, $P_L$ promoter, $P_R$ promoter and other promoters derived form *E. coli* and phages. Artificially designed or modified promoters, such as tac promoter, lacT7 promoter and let I promoter, may also be used.

The recombinant vector may be introduced into bacteria using any technique that can introduce DNA into bacteria. Examples of such techniques include the calcium ion method and electroporation.

When the host cell is yeast, yeast species such as *Saccharomyces cerevisiae*, *Schizosaccharomyces pombe* and *Pichia pastoris* may be used as the host cell. The promoter for use in the yeast hosts may be any promoter that can promote the expression of the desired protein in yeast cells, including gal1 promoter, gal10 promoter, heat shock protein promoter, MFα1 promoter, PHO5 promoter, PGK promoter, GAP promoter, ADH promoter and AOX1 promoter.

The recombinant vector may be introduced into yeasts using any technique that can introduce DNA into yeasts. Examples of such techniques include electroporation, the spheroplast method and the lithium acetate method.

When the host cell is an animal cell, animal cell lines such as monkey cell lines COS-7 and Vero, Chinese hamster ovarian (CHO) cell, mouse L cell, rat GH3 and human FL cell may be used as the host cell. The promoter for use in the animal hosts may be any promoter that can promote the expression of the desired protein in animal cells, including SRα promoter, SV40 promoter, long terminal repeat (LTR) promoter, CMV promoter and cytomegalovirus early gene promoter.

The recombinant vector may be introduced into animal cells using any technique that can introduce DNA into animal cells. Examples of such techniques include electroporation, the calcium phosphate method and lipofection.

When the host cell is an insect cell, cells such as ovarian cells of *Spodoptera frugiperda*, ovarian cells of *Trichoplusia ni* and cultured cells of silkworm ovary may be used as the host cell. Examples of the ovarian cells of *Spodoptera frugiperda* include Sf9 and Sf21. Examples of the ovarian cells of *Trichoplusia ni* include High 5 and BTI-TN-5B1-4 (Invitrogen). Examples of the cultured cells of silkworm ovary include *Bombyx mori* N4.

The recombinant vector may be introduced into insect cells using any technique that can introduce DNA into insect cells. Examples of such techniques include the calcium phosphate method, lipofection and electroporation.

[Culture of Transformant]

Once the recombinant vector incorporating the DNA encoding the desired protein has been introduced into the host cell to form a transformant, the transformant is cultured according to a common culturing technique. The transformant can be cultured using any technique commonly used to culture host cells.

When the transformant is based on a microorganism host, such as *E. coli* and yeast, the culture medium for culturing the transformant may be either a natural medium or a synthetic medium as long as it contains carbon source, nitrogen source, inorganic salts and other nutrients that can be assimilated by the microorganism and as long as it allows the effective growth of the transformant.

The carbon source may be a carbohydrate, such as glucose, fructose, sucrose and starch, an organic acid, such as acetic acid and propionic acid, or an alcohol, such as ethanol and propanol. The nitrogen source may be ammonia, an ammonium salt of an inorganic or organic acid, such as ammonium chloride, ammonium sulfate, ammonium acetate and ammonium phosphate, peptone, meat extracts, yeast extracts, corn steep liquor, or casein hydrolysates. The inorganic salt may be potassium dihydrogenphosphate, dibasic potassium phosphate, magnesium phosphate, magnesium sulfate, sodium chloride, ferrous sulfate, manganese sulfate, copper sulfate or calcium carbonate.

The transformant is cultured under aerobic conditions provided, for example, by shaking the culture, or aerating and agitating the culture. The transformant is typically cultured at a temperature of 30° C. to 37° C. and for a period of 12 hours to 16 hours. The culture is maintained at a pH of 6.0 to 8.0 during the culture period. The pH is adjusted by the use of an inorganic acid, an organic acid, an alkaline solution, urea, calcium carbonate, ammonia or the like. When necessary, ampicillin, tetracycline and other antibiotics may be added to the culture media.

When the expression vector used to transform the microorganism contains an inducible promoter, an inducer may be added to the culture medium as desired. For example, an inducer such as isopropyl-β-D-thiogalactopyranoside may be added to the culture medium when culturing a microorganism transformed with an expression vector containing a lac promoter. Likewise, an inducer such as indoleacrylic acid may be added to the culture medium when culturing a microorganism transformed with an expression vector containing a trp promoter.

When the transformant is based on an animal host cell, the culture medium for culturing the transformant may be any of the commonly used culture media, such as RPMI1640 medium, Eagle's MEM medium, A-MEM medium and DMEM medium, or any of these culture media supplemented with fetal calf serum. The transformant is typically cultured in the presence of 5% $CO_2$ at 30° C. to 37° C. for a period of 1 day to 7 days. When necessary, an antibiotic, such as kanamycin, penicillin, streptomycin, neomycin, hygromycin and blasticidin, may be added to the culture medium.

When the transformant is based on an insect host cell, the culture medium for culturing the transformant may be any of the commonly used culture media, such as TNM-FH medium (Pharmingen), TC-100 medium (Gibco BRL), Sf-900 II SFM medium (Gibco BRL), ExCell400 and ExCell405 (JRH Biosciences). The transformant is typically cultured at 25° C. to 28° C. for a period of 48 hours to 96 hours. When necessary, gentamicin and other antibiotics may be added to the culture medium.

The desired protein may be expressed in the form of a secreted protein or fusion protein. Examples of the protein that can be fused with the desired protein include β-galactosidase, protein A, IgG-binding domain of protein A, chloramphenicol acetyltransferase, poly(Arg), poly(Glu), protein G, maltose-binding protein, glutathione S-transferase (GST), polyhistidine chain (His-tag), S-peptide, DNA-binding protein domain, Tac antigen, thioredoxin, green fluorescent protein, hemagglutinin protein (HA)-tag, FLAG-tag, Myc-tag, T7 gene 10 protein, bovine papilloma virus L1 protein and VSV-G-tag.

[Isolation/Purification of Protein]

The desired protein can be obtained from the culture of the transformant. The term "culture" as used herein is intended to include any of culture supernatant, cultured cells, cultured bacterial cells and lysates of cells or bacterial cells.

To extract the desired protein that accumulates within the cultured cells of the transformant, the cells are first collected by centrifuging the culture. The collected cells are then washed and lysed to obtain the protein. To extract the desired protein that is secreted to the outside of the cultured cells of the transformant, the supernatant of the culture may be used either directly or after removal of the cells or bacterial cells by centrifugation.

The protein thus obtained is then purified. The purification is done by using techniques such as solvent extraction, salting-out with ammonium sulfate, desalting, precipitation with organic solvents, diethylaminoethyl (DEAE)-sepharose, ion-exchange chromatography, hydrophobic chromatography, gel filtration and affinity chromatography.

Alternatively, the desired protein may be produced based on its amino acid sequence by using chemical synthesis techniques such as fluorenylmethyloxycarbonyl (Fmoc) method and the t-butyloxycarbonyl (tBoc) method. A commercially available peptide synthesizer may be used for this purpose.

While the prophylactic/therapeutic agent for neurodegenerative diseases according to the present invention may consist only of an HMGB family protein or a derivative thereof, or a recombinant vector that can express an HMGB family protein or a derivative thereof, it is typically formulated into a preparation with at least one pharmaceutically acceptable carrier, additive, or reagent for introducing DNA or a protein into a cell, using a known technique.

Examples of the pharmaceutically acceptable carrier include water, pharmaceutically acceptable organic solvents, collagen, polyvinyl alcohol, polyvinylpyrrolidone, carboxyvinyl polymers, sodium alginate, water-soluble dextran, carboxymethyl starch sodium, pectin, xanthan gum, gum arabic, casein, gelatin, agar, glycerol, propylene glycol, polyethylene glycol, vaseline, paraffin, stearyl alcohol, stearic acid, human serum albumin, mannitol, sorbitol and lactose.

Examples of the additive to be added to the preparation include fillers, bulking agents, binders, humectants, disintegrating agents, surface active agents, lubricants, excipients, stabilizers, antimicrobial agents, buffers, isotonizing agents, chelating agents, pH adjusters and surfactants. These additives are properly selected depending on the dosage form of the preparation. Of these, the components used in common protein preparations, including stabilizers, antimicrobial agents, buffers, isotonizing agents, chelating agents, pH adjusters and surfactants, are preferred. The reagent for introducing DNA or a protein into a cell is properly selected depending on the introduction technique employed.

Specific examples of each additive are listed below.

Stabilizers: human serum albumin; L-amino acids, such as glycine, cysteine and glutamine; sugars, including monosaccharides such as glucose, mannose, galactose and fructose, sugar alcohols such as mannitol, inositol and xylitol, disaccharides such as sucrose, maltose and lactose, polysaccharides such as dextran, hydroxypropyl starch, chondroitin sulfate and hyaluronic acid, and derivatives thereof; and cellulose derivatives, such as methyl cellulose, ethyl cellulose, hydroxyethyl cellulose, hydroxypropyl cellulose, hydroxypropylmethyl cellulose and carboxymethylcellulose sodium.

Surfactants: surfactants such as polyoxyethylene glycol sorbitan alkyl esters, polyoxyethylene alkyl ethers, sorbitan monoacyl esters and fatty acid glycerides.

Buffers: boric acid, phosphoric acid, acetic acid, citric acid, $\epsilon$-amino caproic acid, glutamic acid and salts thereof (alkali metal salts and alkaline earth metal salts such as sodium salts, potassium salts, calcium salts and magnesium salts).

Isotonizing agents: sodium chloride, potassium chloride, sugars and glycerol.

Chelating agents: sodium edetate and citric acid.

It is desirable that the route of administration and dosage form of the preparation be selected to maximize the effect of the treatment. Typical examples of the administration route include oral routes as well as parenteral routes, including intracerebral, intraperitoneal, intraoral, intrabronchial, intrarectal, subcutaneous, intramuscular and intravenous routes. However, the prophylactic/therapeutic agent for neurodegenerative diseases according to the present invention is preferably administered directly to a target site that requires the prevention/treatment of a neurodegenerative disease. Specifically, the prophylactic/therapeutic agent can be administered to the target site by injection, catheter, incision or other suitable means. Typical examples of the dosage form include sprays, capsules, liposomes, tablets, granules, syrups, emulsions, suppositories, injections, ointments and tapes.

The dose and frequency of administration of the prophylactic/therapeutic agent for neurodegenerative diseases according to the present invention can be properly adjusted depending on the desired effect, and the age and body weight of the patient. The frequency of administration can be properly adjusted depending on the dose, route of administration and dosage form.

Examples of the neurodegenerative diseases that can be prevented/treated by the prophylactic/therapeutic agent of the present invention include, but are not limited to, polyglutamine diseases such as Huntington's disease, spinocerebellar degeneration, dentatorubral-pallidoluysian atrophy and spinobulbar muscular atrophy, as well as other neurodegenerative diseases such as Alzheimer's disease, Parkinson's disease and amyotrophic lateral sclerosis. The prophylactic/therapeutic agent for neurodegenerative diseases according to the present invention are particularly useful in the prevention/treatment of dysfunction and cell death of neurons resulting from neurodegenerative diseases.

A method of the present invention for screening a substance effective in the prevention/treatment of neurodegenerative diseases includes the following steps:

determining whether a test substance inhibits binding of an HMGB family protein or a derivative thereof to an abnormal polyglutamine protein produced in a neurodegenerative disease; and identifying the test substance to be effective in the prevention/treatment of the neurodegenerative disease if the test substance has inhibited the binding.

Alternatively, the method may include the following steps:

determining whether a test substance induces expression of a gene encoding an HMGB family protein or a derivative thereof, and identifying the test substance to be effective in the prevention/treatment of the neurodegenerative disease if the test substance has induced the expression.

Examples of the test substance include, but are not limited to, high-molecular weight compounds, low-molecular weight compounds, cell culture, tissue extracts, antibodies, proteins, peptides, nucleic acids, sugars, inorganic salts, metal complexes and composites thereof. It should be noted that the term "nucleic acid" is intended to include DNA, RNA and analogs and derivatives thereof (such as peptide nucleic acids (PNAs) and phosphorothioate DNA).

Whether a given test substance inhibits binding of an HMGB family protein or a derivative thereof to an abnormal polyglutamine protein produced in a neurodegenerative disease can be determined in the manner described below, although other methods are also possible.

Specifically, an HMGB family protein or a derivative thereof and an abnormal polyglutamine protein are brought into contact in the presence or absence of the test substance. The amount of the HMGB family protein or a derivative thereof bound to the abnormal polyglutamine protein in the presence or absence of the test substance is then measured and the amounts are compared with each other. If the amount of the HMGB family protein or a derivative thereof bound to the abnormal polyglutamine protein is less in the presence of the test substance than in its absence, then the test substance can be determined to inhibit the binding of the HMGB family protein or a derivative thereof to the abnormal polyglutamine protein.

Neurodegenerative diseases such as polyglutamine diseases arise when HMGB family proteins bind to abnormal polyglutamine proteins and become incorporated into inclusion bodies, resulting in a decrease in the amounts of the functional HMGB family proteins in the nuclei. Thus, a substance that inhibits the binding of HMGB family proteins or derivatives thereof to abnormal polyglutamine proteins may have a potential to prevent/treat polyglutamine diseases and other neurodegenerative diseases by preventing the decrease in the amounts of functional HMGB family proteins in the nuclei. In other words, a substance can be screened for the ability to prevent/treat polyglutamine diseases and other neurodegenerative diseases by evaluating its ability to inhibit binding of HMGB family proteins or derivatives thereof to abnormal polyglutamine proteins.

The substance that inhibits the binding of HMGB family proteins or derivatives thereof to abnormal polyglutamine proteins may act on either one or both of HMGB family protein (or derivative thereof) and abnormal polyglutamine protein. The substance that inhibits the binding of HMGB family proteins or derivatives thereof to abnormal polyglutamine proteins also includes those that can inhibit the binding of the two proteins in their unbound state and those that can dissociate the two proteins bound to each other.

An HMGB family protein or a derivative thereof and an abnormal polyglutamine protein may be brought into contact either in vitro or in vivo.

For in vitro contact, each of the HMGB family protein or a derivative thereof and the abnormal polyglutamine protein may be any of the following proteins: (i) an endogenous protein extracted from a cell or tissue expressing the desired protein; (ii) a recombinant protein extracted from a culture of a transformant constructed by introducing a recombinant vector capable of expressing the desired protein into a host cell; and (iii) a chemically synthesized peptide.

For in vivo contact, each of the HMGB family protein or a derivative thereof and the abnormal polyglutamine protein may be any of the following proteins: (i) an endogenous protein present in a cell; and (ii) a recombinant protein present in a cell of a transformant constructed by introducing a recombinant vector capable of expressing the desired protein into a host cell.

To bring an HMGB family protein (or a derivative thereof) and an abnormal polyglutamine protein into contact, the HMGB family protein may be either a wild-type HMGB family protein or a mutant HMGB family protein that retains binding activity to an abnormal polyglutamine protein produced in a neurodegenerative disease. The derivative of HMGB family protein may be any derivative that retains binding activity to an abnormal polyglutamine protein produced in a neurodegenerative disease. Examples of such derivatives include HMGB family proteins having sugar chains added thereto, pharmaceutically acceptable salts of HMGB family proteins, fusion proteins containing HMGB family proteins and labeled HMGB family proteins. Examples of such labels include fluorescent compounds, such as fluorescein, rhodamine, phycoerythrin, Cy dyes, Alexa dyes and BODIPY dyes; chemoluminescent compounds, such as luminol, lucigenin and acridinium esters; enzymes, such as alkaline phosphatase and horseradish peroxidase; bioluminescent compounds, such as luciferase and luciferin; and radioisotopes (RIs), such as $^{32}$P and $^{35}$S.

To bring an HMGB family protein (or a derivative thereof) and an abnormal polyglutamine protein into contact, conditions that can affect the binding of the HMGB family protein or a derivative thereof to the abnormal polyglutamine protein are adjusted so that the binding of the HMGB family protein or a derivative thereof to the abnormal polyglutamine protein will depend on the presence or absence of a test substance.

Examples of the conditions that can affect the binding of an HMGB family protein or a derivative thereof to an abnormal polyglutamine protein include temperature, type of solvents, concentration of HMGB family protein or a derivative thereof and concentration of abnormal polyglutamine protein.

The amount of an HMGB family protein or a derivative thereof bound to an abnormal polyglutamine protein can be measured based on amounts such as the amount of the conjugate of the HMGB family protein or a derivative thereof with the abnormal polyglutamine protein and the amount of signals resulting from the binding of the HMGB family protein or a derivative thereof to the abnormal polyglutamine protein.

For example, the amount of the conjugate of an HMGB family protein or a derivative thereof with an abnormal polyglutamine protein can be measured in the following manner: at least one of the HMGB family protein (or a derivative thereof) and the abnormal polyglutamine protein is labeled and the HMGB family protein (or a derivative thereof) and the abnormal polyglutamine protein are brought into contact. The complex that the HMGB family protein or a derivative thereof forms with the abnormal polyglutamine protein is then separated and the amount of the label in the complex is measured. Specifically, the amount of the conjugate can be determined by GST pull-down assay, as follows: one of the HMGB family protein (or a derivative thereof) and the abnormal polyglutamine protein is labeled with R1 and the other is fused with GST. The HMGB family protein (or a derivative thereof) and the abnormal polyglutamine protein are then brought into contact. The complex of the HMGB family protein or a derivative thereof with the abnormal polyglutamine protein is adsorbed onto a glutathione-Sepharose column. The column is washed and proteins bound to the column are eluted. The eluted proteins are then subjected to SDS-PAGE to separate the complex of the HMGB family protein or a derivative thereof with the abnormal polyglutamine protein. The amount of the conjugate of the HMGB family protein or a derivative thereof with the abnormal polyglutamine protein is then measured based on the amount of the R1 in the complex.

The amount of the conjugate of the HMGB family protein or a derivative thereof with the abnormal polyglutamine protein can be determined by known techniques for protein analysis, including Western blot, immunoprecipitation, ELISA, immunohistochemical staining and other techniques that use an antibody or antibody fragment that can react with the complex of the HMGB family protein or a derivative thereof with the abnormal polyglutamine protein. The term "antibody" is intended to include both monoclonal and polyclonal antibodies. The term "monoclonal and polyclonal antibodies" is intended to include all classes of monoclonal and polyclonal antibodies. The term "antibody fragment" is intended to include Fab fragments, F(ab)'2 fragments and single-chain variable fragment (scFV).

Examples of the signals resulting from the binding of an HMGB family protein or a derivative thereof to an abnormal polyglutamine protein include, but not limited to, expression of reporter genes, fluorescence resonance energy transfer (FRET) and detection of local density change by surface plasmon resonance (SPR) or frequency shift of quartz crystal.

When the signals resulting from the binding of an HMGB family protein or a derivative thereof to an abnormal polyglutamine protein are due to expression of a reporter gene, the amount of the HMGB family protein or a derivative thereof bound to the abnormal polyglutamine protein can be determined by a technique using a transcription activator in the manner described below.

One of the HMGB family protein (or a derivative thereof) and the abnormal polyglutamine protein is fused with the DNA-binding domain of a transcription activator protein GAL4 and the other is fused with the activator domain (TA) of GAL4. The two fusion proteins are expressed in the same cell. If the HMGB family protein (or a derivative thereof) and the abnormal polyglutamine protein do not interact, the GAL4 DNA-binding domain and the activator domain will not come into proximity with each other. If the HMGB family protein (or a derivative thereof) and the abnormal polyglutamine protein interact, the GAL4 DNA-binding domain and the activator domain will come into proximity with each other. In the latter case, if a reporter gene with an upstream activating sequence for galactose (UASG) has been introduced into the yeast cell, its expression level increases. In this way, whether or not the HMGB family protein (or a derivative thereof) and the abnormal polyglutamine protein interact can be determined, as can the degree of interaction.

Examples of the reporter gene include β-galactosidase gene, chloramphenicol acetyltransferase gene, luciferase gene, ampicillin resistance gene, tetracycline resistance gene and kanamycin resistance gene. Examples of the reporter activity include β-galactosidase activity, chloramphenicol acetyltransferase activity, luciferase activity, ampicillin resistance, tetracycline resistance and kanamycin resistance.

When the signals resulting from the binding of an HMGB family protein or a derivative thereof to an abnormal polyglutamine protein are due to fluorescence resonance energy transfer (FRET), the amount of the HMGB family protein or a derivative thereof bound to the abnormal polyglutamine protein can be determined in the manner described below.

One of the HMGB family protein (or a derivative thereof) and the abnormal polyglutamine protein is fused with a fluorescent protein (donor) and the other is fused with another fluorescent protein (acceptor). The HMGB family protein (or a derivative thereof) and the abnormal polyglutamine protein are then brought into contact and the amount of fluorescence resulting from the binding of the HMGB family protein or a derivative thereof to the abnormal polyglutamine protein is measured. Cyan fluorescent protein (CFP) and yellow fluorescent protein may be used as the donor and the acceptor, respectively. Fluorescence resonance energy transfer (FRET) is a phenomenon in which some of the excitation energy of a fluorophore (donor) of a molecule is transferred to a fluorophore (acceptor) of another molecule. The excited fluorophore emits the energy as heat or new fluorescence. In order for the fluorescence resonance energy transfer (FRET) to occur efficiently, the two molecules must be in proximity to each other. For this reason, the phenomenon can be used as an effective means to detect protein-protein interactions in a cell.

Whether a test substance induces the expression of a gene encoding an HMGB family protein or a derivative thereof can be determined in the manner described below, although other methods are also possible.

The test substance and a cell expressing the gene encoding an HMGB family protein or a derivative are brought into contact. The expression level of the gene encoding an HMGB family protein or a derivative is then determined. The expression level after the contact with the test substance is compared with the expression level before the contact with the test substance. If the expression level after the contact with the test substance is higher than the expression level before the contact with the test substance, then it can be determined that the test substance induces the expression of the gene encoding an HMGB family protein or a derivative.

Alternatively, the test substance may be administered to an animal model expressing a gene encoding an HMGB family protein or a derivative thereof. The expression level of the gene in tissues such as brain, spinal cord and peripheral nerve is then determined and the expression level after administration of the test substance is compared with the expression level before administration of the test substance. If the expression level after administration of the test substance is higher than the expression level before administration of the test substance, then it can be determined that the test substance induces the expression of the gene encoding an HMGB family protein or a derivative.

Neurodegenerative diseases such as polyglutamine diseases arise when HMGB family proteins bind to abnormal polyglutamine proteins and become incorporated into inclusion bodies, resulting in a decrease in the amounts of the functional HMGB family proteins in the nuclei. Thus, a substance that induces the expression of a gene encoding an HMGB family protein or a derivative thereof may have a potential to prevent/treat polyglutamine diseases and other neurodegenerative diseases by compensating for the loss of functional HMGB family proteins in the nuclei. In other words, a substance can be screened for the ability to prevent/treat polyglutamine diseases and other neurodegenerative diseases by evaluating its ability to induce the expression of a gene encoding an HMGB family protein or a derivative thereof.

Examples of the substance that can induce the expression of a gene encoding an HMGB family protein or a derivative thereof include substances that can induce transcription of genes into mRNA and substances that can induce translation of mRNA into proteins.

The cell for expressing the gene encoding an HMGB family protein or a derivative thereof may be (i) a cell that expresses the desired protein as an endogenous protein or (ii) a transformant constructed by introducing a recombinant vector capable of expressing the desired protein.

The animal model may be any animal that can express the gene encoding an HMGB family protein or a derivative thereof, including rats, mice, guinea pigs and rabbits. The animal model may be an artificially created transgenic animal that expresses the gene encoding an HMGB family protein or a derivative thereof.

The expression level of the gene encoding an HMGB family protein or a derivative thereof can be determined based on the amount of the HMGB family protein or a derivative thereof or the amount of mRNA.

The HMGB family protein or a derivative thereof may be quantified by using an antibody or antibody fragment specific for the HMGB family protein or a derivative thereof. Examples of the techniques that use such antibodies or antibody fragments include radioimmunoassay (RIA), enzyme immunoassay (EIA), chemiluminescence immunoassay (CLIA) and fluorescence immunoassay (FIA). Alternatively, the HMGB family protein or a derivative thereof may be quantified by measuring the activity of the HMGB family protein or a derivative thereof. The activity of the HMGB family protein or a derivative thereof can be measured by using Western blot, ELISA or any other known technique that uses an antibody or antibody fragment that reacts with the protein. The term "antibody" is intended to include any monoclonal or polyclonal antibody and the term "antibody fragment" is intended to include any fragment that reacts with a protein of interest. Examples of the antibody fragment include Fab fragments, $F(ab)'_2$ fragments and single-chain variable fragment (scFV). The term "react" means that the antibody fragment may react with any part of a protein of interest.

To quantify mRNA, any of the known techniques for gene analysis may be used, including hybridization techniques (such as Northern hybridization, dot blot and DNA microarrays) and gene amplification techniques (such as RT-PCR). One exemplary mRNA quantification technique using RT-PCR is now described. Total RNA is first obtained from the cells expressing a gene encoding an HMGB family protein or a derivative thereof. Poly(A)+RNA (mRNA) is then isolated from the total RNA by techniques such as affinity column chromatography and batch process using oligo dT-cellulose and poly U-sepharose. cDNA is then synthesized and used as a template in a PCR using a primer set that can hybridize with the cDNA. The PCR-amplified fragments are then quantified to measure the amount of mRNA. The PCR is performed under particular conditions so that the amounts of the resulting PCR-amplified fragments reflect the amounts of cDNA used as initial template (for example, PCR is performed for a particular number of cycles during which the PCR-amplified fragments increase exponentially). The quantification of the PCR-amplified fragments may be done by any suitable technique, such as quantification using radioisotopes (RI) and quantification using fluorescent dyes. When RT-PCR is used to quantify the PCR-amplified fragments, a commercially available apparatus such as ABI PRISM 7700 (Applied Biosystems) may be used to enable real-time monitoring of gene amplification process and, thus, more quantitative analysis of the PCR-amplified fragments.

The measured values of the expression levels of a gene of interest are preferably corrected with reference to the measured values of the expression levels of genes whose expression levels do not significantly vary (for example, housekeeping genes such as β-actin gene and GAPDH gene).

The screened substances are useful in the prevention/treatment of polyglutamine diseases, such as Huntington's disease, spinocerebellar degeneration, dentatorubral-pallidoluysian atrophy and spinobulbar muscular atrophy, as well as other neurodegenerative diseases such as Alzheimer's disease, Parkinson's disease and amyotrophic lateral sclerosis. Thus, these substances can be used in the prevention/treatment of dysfunction and cell death of neurons resulting from these neurodegenerative diseases.

EXAMPLES

1. Methods (1) Preparation of Primary Neuron Culture and Nuclear Extraction

Cortical neurons and cerebellar neurons were prepared and cultured according to a known technique (Tagawa, K. et al., J. Neurochem. 89, 974-987. (2004); Fernandez-Funez, P. et al., Nature 408, 101-106. (2000)). The cells were infected with AxCAwt, AxCAwt-HMGB1, AxCAwt-HMGB2, AxCA-htt20Q, AxCA-Htt111Q, AxCA-AT1-30Q or AxCA-AT1-82Q and harvested after 2 days. According to a known technique (Dignam, J. D. et al., Nucleic Acids Res. 11, 1475-1489 (1983); Okamoto, K. et al., Cell 60, 461-472 (1990)), a nuclear extract was prepared from $6 \times 10^7$ cells of the primary neuron culture. Specifically, the cells were suspended in 8 times as much (by volume) of a lysis buffer (20 mM HEPES (pH 7.9), 1 mM EDTA (pH 8.0), 1 mM DTT, 10% glycerol, 0.5 mM spermidine, 1 mM phenylmethylsulfonyl fluoride, 1 µg/ml leupeptin, 1 µg/ml pepstatin A, 0.3 µg/ml antipain and 0.3% NP-40) and homogenized with a Dounce homogenizer type B. The separated nuclei were centrifuged and resuspended in a lysis buffer containing 1M KCl. The suspension was centrifuged at 4° C. for 30 min at 100,000×g. The supernatant was collected and dialyzed against a lysis buffer at 4° C. overnight using a PlusOne™ mini dialysis kit (Amersham Biosciences). The resulting solution was centrifuged at 17,400×g for 15 min and the supernatant was used as the nuclear extract. The extract was stored in aliquots at −80° C.

(2) Two-Dimensional Gel Electrophoresis and Silver Staining

The nuclear extract prepared in the above-described manner was quantified (BioRad). The two-dimensional gel electrophoresis was performed according to a standard method (Amersham Biosciences). Specifically, 50 µg of the nuclear extract was dialyzed against 8M urea and 2% CHAPS for 2 hours (×2). Subsequently, the extract was rehydrated in an immobilized pH gradient gel (IPG, pH 3-10, 18 cm, Amersham Biosciences) strip overnight. Using Electrophoresis Power Supply ESP 3500 XL (Pharmacia Biotech), isoelectric focusing (IEF) was performed at 500V for 1 min, at 3500V for 1.5 hours and at 3500V for 16 hours. The IPG strip was used immediately after IEF or stored at −80° C. After separation by two-dimensional gel electrophoresis, the IPG strip was equilibrated for 10 min with 50 mM Tris-HCl (pH 8.8), 6M urea, 30% glycerol, 2% (w/v) SDS and 0.0125% bromophenol blue (×2). 10 mg/ml dithiothreitol was added for the first equilibration and 25 mg/ml iodoacetamide was added for the second equilibration. Subsequently, the IPG strip was placed on a polyacrylamide gel (ExcelGel XL SDS12-14, 245×180× 0.5 mm) and electrophoresis was performed at 1000V/20 mA for 45 min and then at 1000V/40 mA for 160 min. Immediately after the electrophoresis, the polyacrylamide gel was stained using a silver-staining kit (Amersham Biosciences) and scanned with ImageMaster 2D Elite ver. 4.01 (Amersham Biosciences) to quantify the protein spots.

(3) Trypsin Digestion of Gel and TOF-Mass

To identify the spots by TOF-Mass, two-dimensional electrophoresis was performed again and the gel was stained using Silver Stain MS kit (Wako). The candidate spots on the polyacrylamide gel were destained with Solutions A and B (Silver Stain MS kit, Wako). The gel was incubated for 10 min in 50% acetonitrile (Aldrich) and 50 mM ammonium carbonate (×3). The gel was further incubated for 5 min in 100% acetonitrile and dried for 10 min at room temperature. Subsequently, the gel was digested in 20 µl of a digestion solution (50 ng/µl sequence grade trypsin (Promega), 30% acetonitrile, 50 mM ammonium carbonate) overnight at 30° C. The gel was then dried under vacuum for 30 min and redissolved in 0.1% trifluoroacetic acid (TFA). The solution was passed through ZipTip (Millipore) to collect peptides. For desalting and purification, the collected peptides were washed three times with 0.1% TFA, eluted with 1 µl of an eluant (10 µg/µl α-cyano-4-hydroxycinnamic acid (CHCA), 50% acetonitrile, 0.1% TFA) and subjected to MALDI-TOF MS analysis on SHIMAZU/KRATOS MALDI-TOF/MS AXIMA-CRF (SHIMAZU BIOTECH). The resulting spectral files were analyzed with AXIMA-CFR (S/W Version 2) and the results were submitted to MASCOT research engine (http://www.matrixscience.com) (cross-referenced to NCBI database) to identify the corresponding proteins.

(4) Immunocytochemistry

HeLa cells ($5 \times 10^4$) and cortical primary neurons ($1.7 \times 10^6$) were cultured in a 6 cm dish and fixed 2 days after infection with an adenoviral vector (Tagawa, K. et al., J. Neurochem. 89, 974-987. (2004)). Anti-Htt goat polyclonal antibody (N-18; 1:100; Santa Cruz), anti-AT1 goat polyclonal antibody (H21; 1:100; Santa Cruz), anti-HMGB1 rabbit polyclonal antibody (1:1000; BD Bioscience) and anti-HMGB2 rabbit polyclonal antibody (1:200; BD Bioscience) were used as primary antibodies, and Alexa Flour 488-labeled anti-goat antibody (Molecular Probes) and Cy3 anti-rabbit antibody (Jackson Immuno-Research) were used as secondary antibodies. Cells were first incubated with H21 or N-18 at room temperature for 1 hour and then with Alexa Flour 488-labeled anti-goat antibody (secondary antibody) at room temperature for 1 hour. For double staining, cells were incubated with 5% skim milk for 30 min, followed by incubation with anti-HMGB1 antibody or anti-HMGB2 antibody at 4° C. overnight and subsequently with Cy3 anti-goat antibody (secondary antibody) at room temperature for 1 hour.

(5) Western-Blot Analysis

Samples were dissolved in a sample-loading buffer (62.5 mM Tris/HCl (pH6.8), 2% (w/v) sodium dodecyl sulfate (SDS), 2.5% (v/v) 2-mercaptoethanol, 5% (v/v) glycerol, 0.0025% (w/v) bromophenol blue). The solution was heated at 100° C. for 3 min. Following electrophoresis, the gel was transferred to a polyvinylidene difluoride membrane (Fine Trap, Nihon Eido) and the membrane was incubated with primary antibody and then with horseradish peroxidase-conjugated secondary antibody for 1 hour. Subsequently, the membrane was visualized by enhanced chemiluminescence Western Blotting Detection System (Amersham Biosciences). Primary antibodies were diluted as follows: 1C2 (1:2000; Chemicon), CAG53b (1:2000) (Scherzinger, E. et al., Cell. 90, 549-558. (1997)), HMGB1 (1:5000; BD Biosciences), HMGB2 (1:2000; BD Biosciences), AT1H21 (1:500; Santa Cruz) and GFP (1:1000; Clontech).

(6) Immunoprecipitation

HeLa cells ($1\times10^6$) in a 10 cm dish were transfected with pEGFP-N1, pEGFP-N1-HMGB1 or pEGFP-N1-HMGB2 using SuperFect (invitrogen). The cells were also infected with adenoviral vectors (AxCAwt, AxCA-HMGB1, AxCA-HMGB2, AxCA-htt20Q, AxCA-htt111Q, AxCA-AT1-30Q or AxCA-AT1-82Q) in the same manner as described above. Immunoprecipitation was performed according to a known technique (Okazawa, H. et al., Neuron. 34, 701-713. (2002)). Specifically, collected HeLa cells were incubated at 4° C. in TNE buffer (10 mM Tris-HCl (pH7.8), 10% NP-40, 0.15M NaCl, 1 mM EDTA) for 1 hour and were then centrifuged at 17,400×g for 20 min. The supernatant was preincubated with protein G-Sepharose (Amersham Biosciences) at 4° C. for 2 hours and then centrifuged. The supernatant was incubated with anti-HMGB1 antibody (1:600, BD Biosciences), anti-HMGB2 antibody (1:600, BD Biosciences) or anti-GFP antibody (1:600, Clontech) overnight and was subsequently incubated with protein G-Sepharose for 2 hours. The protein G beads were collected by centrifugation (2,000×g) for 5 min and washed 5 times with TNE buffer. The bound proteins were eluted with a sample buffer, separated by SDS-PAGE, and blotted with CAG53b antibody (Scherzinger, E. et al., Cell. 90, 549-558. (1997)).

(7) Pull-Down Assay

GST, GST-HMGB1/2, HMGB1/2-ΔC1 and HMGB1/2-ΔC2 fusion proteins were expressed and purified according to the protocol provided by the manufacturer (Glutathione Sepharose 4 FastFlow; Amersham Pharmacia Biotech). Specifically, *E. coli* BL21 was transfected with pGEX-3X, pGEX-3X-HMGB1/2, pGEX-3X-HMGB1/2-ΔC1 or pGEX-3X-HMGB1/2-ΔC2 plasmids and cultured. The fusion proteins were induced with IPTG (1.0 mM). The cells were collected and suspended in PBS containing 1 mM EDTA and 1 mM PMSF. The suspension was sonicated. Triton-100 (1%) was then added and the suspension was incubated at 4° C. for 30 min and then centrifuged at 10,000×g for 5 min. The GST fusion proteins in the supernatant were purified using glutathione-Sepharose 4B beads (Amersham Biosciences) and eluted with glutathione buffer (50 mM Tris-HCl, 10 mM glutathione-reduced form). The GST fusion proteins were then collected by centrifuging the supernatant at 500×g and detected by Western blot. For the pull-down assay, IP samples were preincubated with GS4B beads at 4° C. for 1 hour under agitation. The supernatant was collected by centrifugation and incubated overnight with GST, GST-HMGB1/2, HMGB1/2-ΔC1 or HMGB1/2-ΔC2. The GS4B beads were collected by centrifugation (2,000×g for 5 min) and washed 5 times with TNE buffer. The bound proteins were eluted with a sample buffer, separated by SDS-PAGE, and blotted with CAG53b antibody (Scherzinger, E. et al., Cell. 90, 549-558. (1997)).

(8) Immunohistochemistry of the Brain of Transgenic Mice

Brain tissue was prepared from 64-week-old R6/2 huntingtin transgenic mice (Scherzinger, E. et al., Cell. 90, 549-558. (1997)), 40-week-old SCA1(154Q/2Q) knock-in mice (Watase, K. et al., Neuron. 34, 905-919. (2002)) and their littermates. The sections were deparaffined, rehydrated, and pretreated with 0.1M sodium acetate buffer (pH 7.0). For SCA1(154Q/2Q) knock-in mice, the sections were incubated with 11NQ (anti-polyglutamine rabbit polyclonal antibody, 1:100, ref35) and then with Alexa Flour 488-labeled anti-rabbit antibody (Molecular Probes) at room temperature for 1 hour. For huntingtin transgenic mice, the sections were treated with 0.3% hydrogen peroxide for 30 min to block endogenous peroxidase activity and were then incubated with each of anti-Htt goat polyclonal antibody (N-18; 1:20; Santa Cruz) and anti-goat HRP-labeled secondary antibody at room temperature for 1 hour. Subsequently, the sections were detected with Fluororescein Amplification Reagent (1:50; TSA BIOTIN SYSTEM; PerkinElmer) at room temperature for 5 min. For double staining, the sections were blocked with 5% skim milk-PBS and incubated with anti-HMGB1 rabbit polyclonal antibody (1:100; BD Bioscience) or anti-HMGB2 rabbit polyclonal antibody (1:50; BD Bioscience) at 4° C. overnight and subsequently with Cy3 anti-rabbit secondary antibody at room temperature for 1 hour. The signal intensity per $\mu m^2$ was measured using Aquacosmos (HAMAMATSU).

(9) Cloning and Construction of Plasmids

Plasmids pBS-HMGB1/2, pEGFP-N-1-HMGB1/2, pCI-HMGB1/2 and pGEX-3X-HMGB1/2 were constructed by inserting full-length rat HMGB1 cDNA (SEQ ID NO: 9) or HMGB2 cDNA (SEQ ID NO: 11) into plasmids pBluescript II SK+ (Clontech), pEGFP-N1 (Clontech), pCI-neo (Clontech) and pGEX-3X (Amersham), respectively. pGEX-3X-HMGB1-ΔC1/2 and pGEX-3X-HMGB2-ΔC1/2 were constructed by inserting HMGB1 cDNA or HMGB2 cDNA lacking C-terminal region into pGEX-3X. Each construct was confirmed by sequence analysis and the expression levels of encoded proteins were determined by Western blot. The C-terminal region-lacking HMGB1 cDNA contained in pGEX-3X-HMGB1-ΔC1 contains a region encoding amino acids 1-186 of rat HMGB1 (215 amino acids, SEQ ID NO: 10) while the C-terminal region-lacking HMGB1 cDNA contained in pGEX-3X-HMGB1-ΔC2 contains a region encoding amino acids 1-146 of rat HMGB1 (215 amino acids, SEQ ID NO: 10). The C-terminal region-lacking HMGB2 cDNA contained in pGEX-3X-HMGB2-ΔC1 contains a region encoding amino acids 1-186 of rat HMGB2 (210 amino acids, SEQ ID NO: 12) while the C-terminal region-lacking HMGB2 cDNA contained in pGEX-3X-HMGB2-ΔC2 contains a region encoding amino acids 1-165 of rat HMGB2 (210 amino acids, SEQ ID NO: 12).

(10) Construction of Adenovirus and Confirmation of Expression

Adenoviruses AxCA-HMGB1 and AxCA-HMGB2 were constructed according to the instruction manual provided by the manufacturer (Takara). Specifically, HMGB1 and HMGB2 cDNA fragments were excised from pBS-HMGB1 and pBS-HMGB2 as XhoI-EcoRI fragments, respectively. The cDNA fragments were then blunt-ended using Blunting kit (TOYOBO) and subcloned into the SwaI site of pAxCAwt (Takara). The expression of HMGB1 and HMGB2 proteins by these adenoviruses was confirmed prior to use. The adenoviral vectors AxCA-htt111Q and AxCA-htt20Q contain human Htt exon I to which a trinucleotide (CAG) repeat encoding a polyglutamine tract of 111 or 20 residues has been added. The adenoviral vectors AxCA-AT1-30Q and AxCA-AT1-82Q contain full-length human AT1 cDNA to which a trinucleotide (CAG) repeat encoding a polyglutamine tract of 30 or 82 residues has been added. These adenoviral vectors were constructed according to a known technique (Tagawa, K. et al., J. Neurochem. 89, 974-987. (2004)).

(11) Primary Culture of Purkinje Cells

Cerebellar neurons were prepared from 20-21-day-old Wistar rat fetuses and cultured by a known technique (Hirai, H. et al., J. Neurosci. 20, 5217-5224. (2000)) to analyze the growth and dendritic differentiation of Purkinje cells. Specifically, the cells were plated at $2\times10^5$ cells/per well in a poly-L ornithine-coated 12-well plate in 40 µl of a plating medium ($5\times10^6$ cells/ml, DMEM/F-12 supplemented with 10% FBS). Three hours after plating, 1 ml of FBS-free culture medium was added. Seventeen days after plating, the cerebellar neurons were infected with the adenoviral vectors and fixed after 4 days. For morphological analysis of Purkinje cells, the cells were immunostained with anti-mouse monoclonal calbindin-28k antibody (1:200, Sigma-Aldrich) at room temperature for 1 hour.

(12) Cell Death Assay

For the cell death assay of primary cortical neurons, neurons were plated in a 6-well plate ($1.6 \times 10^5$ cells/well) and infected with AxCA, AxCA-HMGB1, AxCA-HMGB2, AxCA-htt20Q or AxCA-htt111Q (m.o.i 300) after 3 days. After 48 hours, propidium iodide (PI) diluted 1:1000 was added to the culture medium and the culture was incubated for 20 min. Subsequently, the neurons were washed with 0.1M phosphate-buffered saline containing 1% paraformaldehyde and PI-positive cells were counted.

(13) BrU Transcription Assay

Three days after infection with AxCA, AxCA-HMGB1, AxCA-HMGB2, AxCA-htt20Q, AxCA-htt111Q, AxCA-AT1-30Q or AxCA-AT1-82Q, the primary neurons were incubated with BrU for 3 hours and fixed in 0.1M phosphate-buffered saline containing 1% paraformaldehyde. The cells were then stained with anti-BrU mouse monoclonal antibody (1:200, Sigma-Aldrich). BrU immunoreactivity was quantified by a known technique (Hoshino, M. at al., Biochem Biophys Res Commun. 313, 110-116. (2004)).

(14) *Drosophila* genetics

Flies were cultured and crossed at 25° C. P{GMR-GAL4} (BL8121), P{GMR-HD120Q} (BL8533) (Jackson, G. R. et al., Neuron. 21, 633-642. (1998)) were obtained from Bloomington Stock Center. Transgenic flies expressing human mutant AT1 ($y^1w^{118}$ UAS: SCA182Q[F7]; GMR-GAL4) are known (Fernandez-Funez, P. et al., Nature. 408, 101-106. (2000)). UAS-HMGB1 transgenic flies were created by cloning rat cDNA into the pUAST transformation vector and introducing the DNA construct into split w(cs10) eggs (Dura, J. M. et al., J. Neurogenet. 9, 1-14. (1993)) (Rubin, G. M. et al., Science. 218, 348-353. (1982)). To compare the effects of HMGB1 on the photoreceptor neuron degeneration and/or the characteristic eye phenotypes induced by the expression of human htt120Q or SCA182Q between the F1 populations, male $y^1w^{118}$ UAS: SCA182Q[F7]; GMR-GAL4 or male GMR-HD120Q; GMR-GAL4 was crossed with female UAS-HMGB1/Cyo. To evaluate the genotype, crossing with different males was individually carried out at least 4 times.

(15) *Drosophila* Histology

To obtain sections of fly photoreceptor neurons, the heads of adult flies (0-10 days) were fixed in 2% formaldehyde and 0.1M phosphate buffer (PB) containing 2.5% glutaraldehyde at 4° C. overnight. Subsequently, the heads were fixed in 1% osmium at room temperature for 3 hours and dehydrated in ethanol. The heads were then embedded in Epon and vertical and transverse sections (2 µm) were prepared. The sections were stained with toluidine blue. For scanning electron microscopy (SEM), the fly heads were fixed in 0.1M PB containing 2.5% glutaraldehyde and then in 0.1M PB containing 1% osmium (each fixation at 4° C. for 2 hours). The heads were then dehydrated in ethanol and critical-point-dried. At least five individuals were used for each genotype and at each time point.

2. Results and Discussion

To understand patterns of the nuclear dysfunction induced by mutant polyglutamine proteins, it is necessary to quantify the changes in the amounts of the domains of soluble nuclear proteins involved in transcription, RNA modification or chromatin remodeling. However, while much is known about the components of nuclear inclusion bodies, the changes that the soluble nuclear proteins undergo in the nucleus still remain unclear.

Thus, a proteome analysis was conducted on soluble proteins in primary neurons expressing mutant huntingtin (Htt111Q) or mutant ataxin-1 (AT1-82Q). Huntingtin (Htt) and ataxin-1 (AT1) are the products of the causative genes of Huntington's disease (HD) and spinocerebellar ataxia type 1 (SCA1), respectively.

To isolate the soluble proteins from the nuclear matrix, the procedure based on a standard protein purification protocol (Dignam, J. D. et. al., Nucleic Acids Res. 11, 1475-1489 (1983)) was performed, which comprised the following steps:

1: Infecting primary neurons with adenovirus.
2: Isolating nuclei from $6 \times 10^7$ neurons.
3: Suspending nuclei in 1M KCl buffer.
4: Centrifuging at 100×k g
5: Dialysis
6: Centrifuge
7: Supernatant
8: Two-dimensional electrophoresis
9: MALDI-TOF/MS AXIMA-CRF (SHIMAZU BIO-TECH, Japan)
10: MASCOT (MASCOT is a search engine which uses mass spectrometry data to identify proteins from primary sequence databases).

The nucleus was isolated from neurons two days after transfection with adenoviral vectors designed to express the polyglutamine proteins (before cell death occurs). Without perforating the nuclear membrane, nuclear proteins were eluted out by the action of osmotic pressure created by potassium chloride. Western blot analysis was performed to confirm that aggregates were removed completely (FIG. 1). As expected, aggregates of Htt protein were observed in the nuclear pellet (accumulated in the upper part of the gel) (indicated by solid line in FIG. 1). Most of AT1 protein was also removed (indicated by arrows in FIG. 1). The nuclear extract was dialyzed with a low potassium buffer and centrifuged to separate insoluble proteins that can permeate through the nuclear membrane. After centrifugation, the supernatant was subjected to two-dimensional electrophoresis (Lanes 2 in FIG. 1). The soluble nuclear protein fraction did not contain any of large aggregates, small intermediates or degenerates of the mutant proteins (Lanes 2 in FIG. 1). The mutant polyglutamine proteins were separated in the nuclear fraction or the insoluble fraction (among other nuclear extracts) (Lanes 1 and 3 in FIG. 1). The insoluble fractions containing the mutant proteins were not used in this experiment. The estimated molecular weight of AT1 and Htt proteins were 93.6 and 21.5 kD, respectively. Thus, the major bands larger than the estimated molecular weights are due to delayed migration of the mutant proteins in SDS-PAGE caused by conformational change (FIG. 1). The formation of oligomers or multimers may also have resulted in the high molecular weight bands in the insoluble fractions (Lanes 1 and 3 in FIG. 1). On the other hand, the low molecular weight bands are considered to correspond to the degraded products. FIG. 1 shows the results of Western blot analysis using CAG53b antibody (Sherzinger, E. et al. Cell. 90, 549-558. (1997)) performed on whole cell lysates (Lanes 1) of cortical neurons expressing mutant polyglutamine protein AT1-82Q or cortical neurons expressing mutant polyglutamine protein Htt111Q, as well as the results for soluble protein fractions (Lane 2) and insoluble fractions (Lane 3) of the nuclear extracts prepared from the same cells. Characteristic bands for each polyglutamine protein are indicated by arrows (Lane 1 of AT1-82Q and Lane 1 of Htt111Q). High molecular weight aggregates of mutant Htt (accumulated in the upper part of the gel) are indicated by solid line. The major bands of AT1-82Q (indicated by arrows in Lane 1) are not observed in the nuclear extracts (Lanes 2 and 3). This suggests that AT1-82Q could not pass through the nuclear membrane pores and thus remained within the nucleus. On the other hand, Htt111Q was insoluble and precipitated during preparation although the protein had been extracted from the nucleus (indicated by arrows in Lane 3). The mutant proteins were not detected in the soluble nuclear protein fractions.

Soluble nuclear proteins obtained from primary cortical and cerebellar neurons expressing normal or mutant polyglutamine proteins are separated on a two-dimensional gel. Soluble proteins from uninfected neurons and neurons infected with AXCA mock virus were used as controls. The analysis was performed independently in triplicates. About 400 spots were detected on the two-dimensional gel after silver staining and were sequentially numbered. Using ImageMaster 2D Elite ver.4.01 (Amersham Biosciences), the signal intensity was determined for each of the 400 spots and compared between uninfected neurons and those infected with a vector designed to express normal polyglutamine protein (AxCA-htt20Q), a vector designed to express mutant polyglutamine protein (AxCA-htt111Q), or an AxCA mock vector. To analyze the differences between neurons expressing normal polyglutamine proteins and those expressing mutant polyglutamine proteins, the spots that differ significantly in signal intensity (twice or more) were chosen for the TOF-MASS analysis. Typical spots are shown enlarged (FIG. 2A, 2B). The protein in this spot is expressed at a significantly lower level in the cortical neurons expressing mutant Htt (Htt111Q) as compared to the cortical neurons expressing normal Htt (Htt20Q). The peptide mass foot print from this spot was further analyzed using Mascot Research Engine. The results demonstrated that the spot was HMGB1. Similar analyses were performed on cortical neurons expressing normal AT1 (AT1-30Q) or mutant AT1 (AT1-82Q) and on cerebellar neurons expressing normal AT1 or mutant AT1 or expressing normal Htt or mutant Htt. Two hundreds (200) spots were then excised from the gels and similarly subjected to TOF-MASS analysis. Some of the spots corresponded to several candidate proteins and were identifiable based on isoelectric points. Of these spots, 59 proteins were ultimately identified. The ratio of the signal intensity between the neurons expressing normal polyglutamine proteins and the neurons expressing abnormal polyglutamine proteins was determined for these spots. The results revealed that mutant Htt and AT1 caused a constant decrease in the amount of HMGB family protein in patients with HD or SCA1 (Table 1). As shown in Table 1, HMGB1 and HMGB 2 were decreased both in cerebellar neurons expressing mutant AT1 and in cortical neurons expressing mutant Htt. Cerebellar and cortical neurons are adversely affected in SCA1 and HD, respectively. In contrast, HMGB proteins were not decreased in cortical neurons expressing mutant AT1. Cortical neurons are not adversely affected in SCA1. The decrease in the amount of HMGB1 and HMGB 2 in the soluble fractions of nuclear extract was also confirmed by Western blot (data not shown).

TABLE 1

|  | AT1-82Q/AT1-30Q | | Htt111Q/Htt20Q | |
| --- | --- | --- | --- | --- |
|  | Cortex | Cerebellum | Cortex | Cerebellum |
| HMGB1 (pI 5.86) | 0.53 | 0.74 | 0.49 | 1.54 |
| HMGB1 (pI 5.99) | 1.11 | 0.97 | 0.56 | 2.13 |
| HMGB2 (pI 8.21) | 0.40 | 0.57 | 0.18 | 4.34 |
| HMGB2 (pI 8.62) | 1.20 | 0.42 | 0.10 | 1.74 |

To analyze the relationship between HMGB family proteins and mutant polyglutamine proteins, immunohistochemistry of primary neurons expressing mutant polyglutamine proteins was performed. HMGB1 and HMGB 2 were co-localized with mutant Htt or AT1 in the inclusion bodies of cortical neurons (FIG. 3A, 3B). In cells with mutant polyglutamine aggregates, HMGB1 and HMGB 2 were decreased in the nuclear matrix surrounding the inclusion bodies (FIG. 3A, 3B). Similar co-localization was observed for exogenous HMGB and overexpressed mutant polyglutamine proteins in HeLa cells (data not shown). This suggests that mutant polyglutamine proteins interact with HMGB1 and HMGB 2. FIGS. 3A and 3B show immunohistochemistry of adenoviral vector-infected primary cortical neurons using anti-HMGB protein antibodies and anti-Htt (N18) or anti-AT1 (H21) antibodies (3 days after infection). In the figures, blank arrows indicate cells with nuclear inclusion bodies in which HMGB proteins in the nuclear matrix were decreased.

Immunoprecipitation and pull-down assay were performed to test whether HMGB family proteins and polyglutamine proteins interact. Prior to immunoprecipitation, the specificity of various anti-polyglutamine antibodies was characterized by Western blot analysis (data not shown). CAG53b antibody reacted with normal and mutant polyglutamine proteins (AT1 and Htt). Anti-AT1 antibody (H21) detected normal and mutant AT1 but not Htt. 1C2 antibody preferentially reacted with mutant Htt and AT1. In light of these specificities, immunoprecipitation and pull-down assay were performed using CAG53b.

Figure 4A:
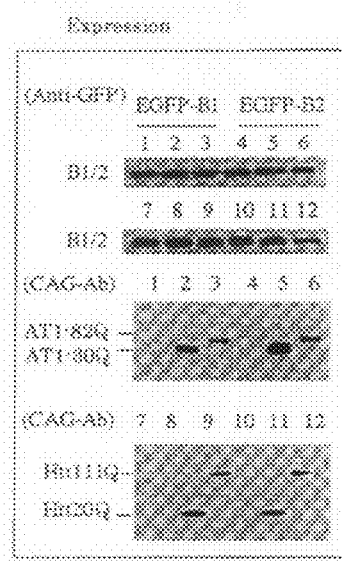
FIG. 4A shows the results of Western blot of total cell lysates using CAG53b antibody and anti-GFP antibody.
Figure 4B:
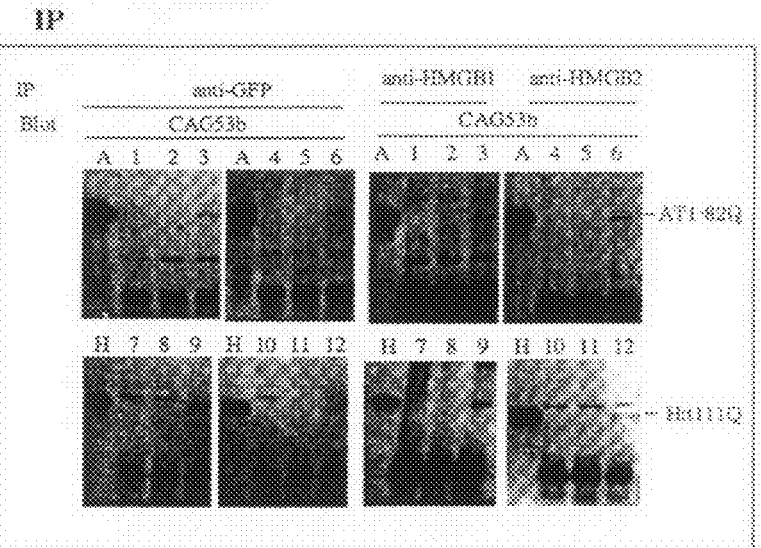
FIG. 4B shows the results of anti-CAG53b Western blot of immunoprecipitation using anti-HMGB or anti-EGFP antibody.
Figure 5A:
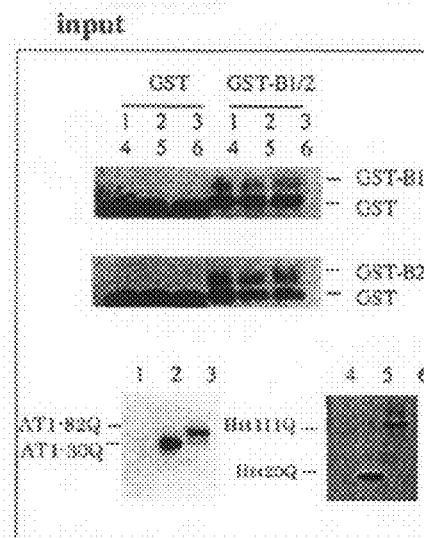
FIG. 5 shows the results of a pull-down assay performed using HeLa cells expressing polyglutamine proteins. Immunoblotting results of both the total cell lysates (A) and the proteins bound to the beads (B) are shown.
Figure 5B:
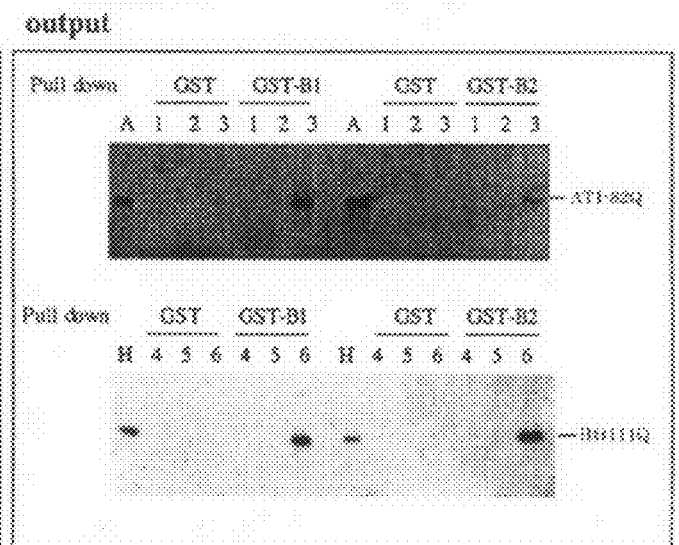

A plasmid pEGFP-N-1-HMGB1/2 was transfected into Hela cells and the cells were infected with an adenoviral vector designed to express normal or mutant polyglutamine protein. The cells expressed normal or mutant polyglutamine protein. The expression levels of polyglutamine protein and HMGB-EGFP protein were checked by Western blot using CAG53b antibody and anti-GFP antibody (FIG. 4A). Immunoprecipitation was performed using anti-HMGB or anti-EGFP antibody. The mutant polyglutamine protein co-precipitated with HMGB1 and HMGB2, but normal polyglutamine protein did not co-precipitate therewith (FIG. 4B). The pull-down assay using HeLa cells expressing polyglutamine protein indicated interaction between mutant polyglutamine protein and HMGB protein (FIG. 5A, 5B). In FIGS. 4A and 4B, Lane 1 is the result of pEGFP-N-1-HMGB1 transfection and AxCA infection; Lane 2 is the result of pEGFP-N-1-HMGB1 and AxCA-AT1-30Q infection; Lane 3 is the result of pEGFP-N-1-HMGB1 transfection and AxCA-AT1-82Q infection; Lane 4 is the result of pEGFP-N-1-HMGB2 transfection and AxCA infection; Lane 5 is the result of pEGFP-N1-HMGB2 transfection and AxCA-AT1-30Q infection; Lane 6 is the result of pEGFP-N1-HMGB2 transfection and AxCA-AT1-82Q infection; Lane 7 is the result of pEGFP-N1-HMGB1 transfection and AxCA infection; Lane 8 is the result of pEGFP-N1-HMGB1 transfection and AxCA-htt20Q infection; Lane 9 is the result of pEGFP-N1-HMGB1 transfection and AxCA-htt111Q infection; Lane 10 is the result of pEGFP-N1-HMGB2 transfection and AxCA infection; Lane 11 is the result of pEGFP-N1-HMGB2 transfection and AxCA-htt20Q infection; Lane 12 is the result of pEGFP-N1-HMGB2 transfection and AxCA-htt111Q infection; and 'A' denotes AT1-82Q and 'H' denotes Htt111Q. In FIGS. 5A and 5B, Lane 1 is the result of AxCA infection; Lane 2 is the result of AxCA-AT1-30Q infection; Lane 3 is the result of AxCA-AT1-82Q infection; Lane 4 is the result of AxCA infection; Lane 5 is the result of AxCA-htt20Q infection; Lane 6 is the result of AxCA-htt111Q infection; and 'A' denotes AT1-82Q and 'H' denotes Htt111Q.

Figure 6A:
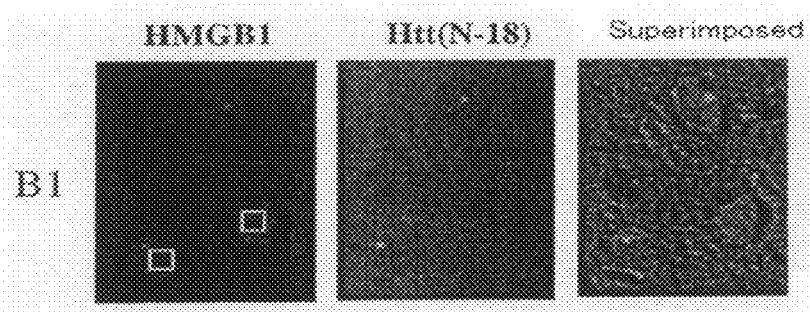
FIG. 6A shows the results of immunohistochemistry using mutant Htt transgenic mice using the antibodies shown at the top.
Figure 6B:
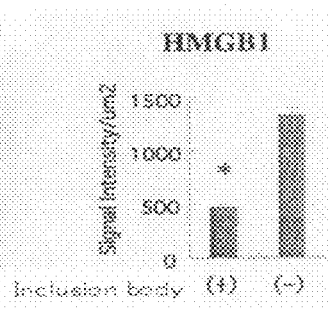
FIG. 6B shows the results of quantitative analysis of signal intensity in FIG. 6A.
Figure 6C:
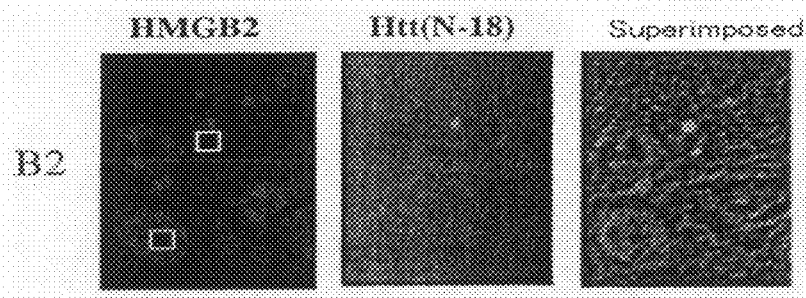
FIG. 6C shows the results of immunohistochemistry of mutant Htt transgenic mice using the antibodies shown at the top.
Figure 6D:
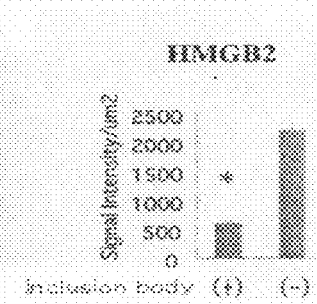
FIG. 6D shows the results of quantitative analysis of signal intensity in FIG. 6C.

Furthermore, immunohistochemical analysis was performed using mutant Htt transgenic mice and AT1 knock-in mice. The results obtained for mutant Htt transgenic mice indicated co-localization of HMGB and mutant polyglutamine proteins in the inclusion bodies and a decrease in the amount of HMGB in the nuclear matrix of neurons with inclusion bodies (FIG. 6A, 6B, 6C, 6D). FIGS. 6A and 6C indicate that HMGB is co-localized with the mutant Htt protein in the inclusion bodies of striatal neurons in Htt transgenic mice. The striate body of 64-week old R6/2 mice was stained with anti-Htt (N-18) and HMGB antibodies. FIGS. 6B and 6D show the results of the quantitative analysis of signal intensity of nuclear matrix obtained from 100 or more neurons. The results indicate a decrease in the amount of HMGB in the nuclear matrix of inclusion body-positive cells (*: $p<0.01$, Student t-test). In contrast to the mutant Htt transgenic mice, inclusion bodies were hardly observed in the neurons of the AT1 knock-in mice, as is the case with Purkinje cells. On the other hand, numerous inclusion bodies were observed in the hippocampus and cerebral cortex (data not shown). Immunohistochemistry of AT1 knock-in mice (AT1-KI) revealed that HMGB was decreased in the nuclear matrix of Purkinje cells and granulocytes (FIG. 7A, 7B, 7C). FIG. 7A shows the results of immunohistochemical analysis of AT1 knock-in mice using 11NQ antibody. FIGS. 7B and 7C show the results of the quantitative analysis of signals obtained from 100 or more cells (*: $p<0.01$, *: $p<0.05$, Student t-test). These results are consistent with the decrease in the amount of HMGB proteins in the soluble nuclear protein fractions of primary neurons expressing mutant AT1 protein. The HMGB levels in the control mice were lower in Purkinje cells than in the other neurons. In the Purkinje cells of AT1 knock-in mice, the nuclear signal of HMGB was even lower than the cytoplasm signal (FIG. 7A). These results suggest that although the incorporation of HMGB into inclusion bodies is not essential for the decrease of HMGB, their decrease is a common characteristic observed in the neurons of the HD and SCA1 mouse models. While the interaction between HMGB and non-aggregated polyglutamine proteins (monomers or oligomers) is a key factor in the decrease in HMGB, the manner in which the protein complexes degenerate is considered to differ between the two mouse models.

Figure 8A:
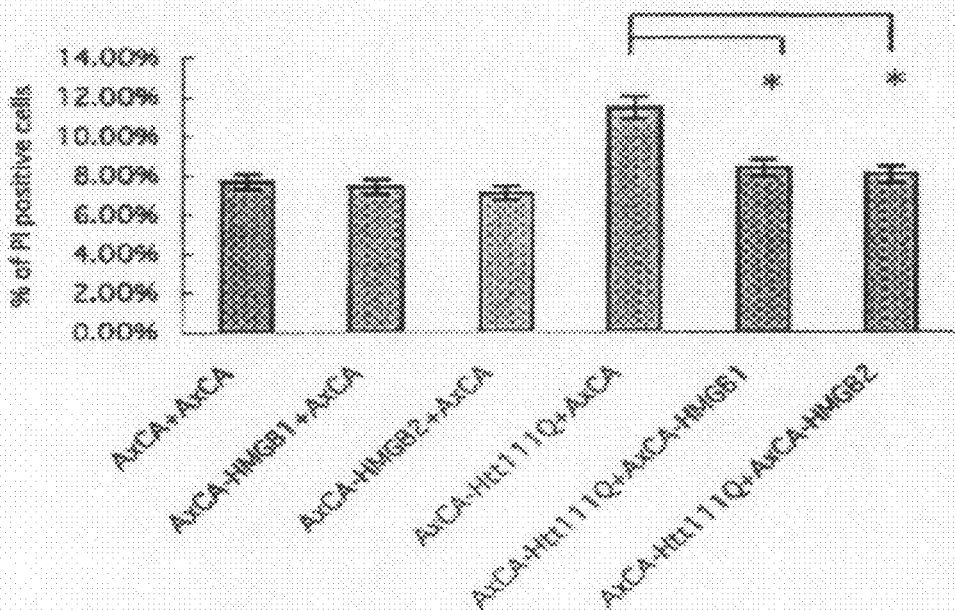
FIG. 8A shows the suppression of mutant Htt-induced cell death of cortical neurons by HMGB.
Figure 8B:
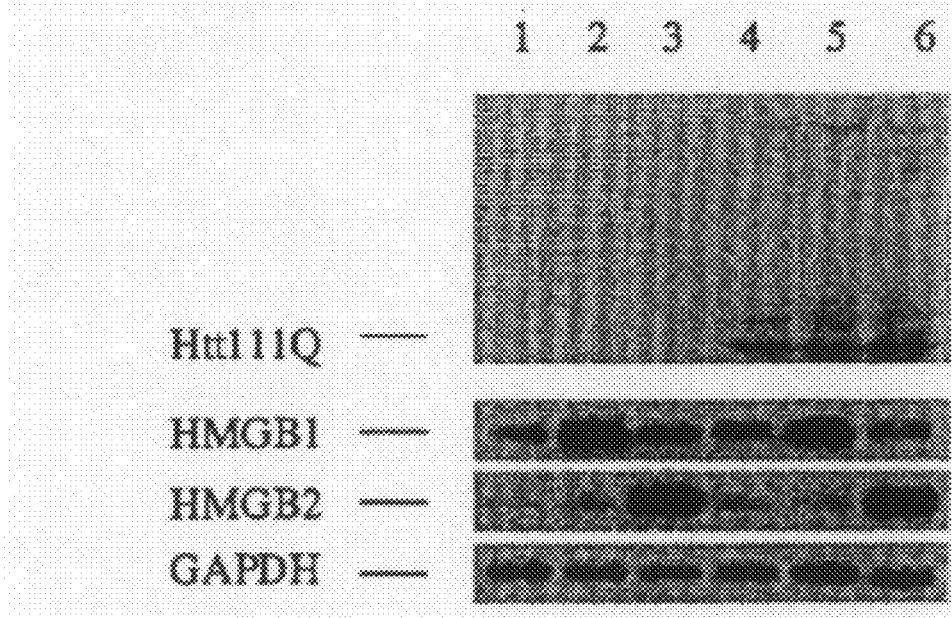
FIG. 8B shows the results of Western blot confirming the expression levels of Htt and HMGB proteins in primary cortical neurons.

To examine how the decrease in HMGB affects polyglutamine diseases, it was tested whether primary neurons would be protected from the polyglutamine protein toxicity by providing HMGB using adenoviral vectors. First, the effect of HMGB proteins on Htt-induced cell death of cortical neurons was observed. The cell death was decreased to the back ground level (FIG. 8A). This suggests that HMGB can suppress Htt-induced cell death. The expression of mutant Htt with HMGB was confirmed (FIG. 8B). Primary neurons derived from Htt transgenic mice were used in this assay. FIG. 8A shows the suppression of mutant Htt-induced cell death of cortical neurons by HMGB. The cell death rate was calculated from the proportion of PI positive cells 3 days after infection with the adenoviral vectors. As shown in FIG. 8A, the cell death was increased by the adenoviral vector expressing Htt111Q. The increase was suppressed by co-infection with AxCA-HMGB1 or 2, but not by co-infection with the mock adenoviral vector. FIG. 8B shows the results of Western blot confirming the expression levels of Htt and HMGB proteins in the primary cortical neurons. In FIG. 8B, Lane 1 is the result of AxCA and AxCA co-infection; Lane 2 is the result of AxCA-HMGB1 and AxCA co-infection; Lane 3 is the result of AxCA-HMGB2 and AxCA co-infection; Lane 4 is the result of AxCA and AxCA-Htt111Q co-infection; Lane 5 is the result of AxCA-HMGB1 and AxCA-Htt111Q co-infection; and Lane 6 is the result of AxCA-HMGB2 and AxCA-Htt111Q co-infection.

Figure 9A:
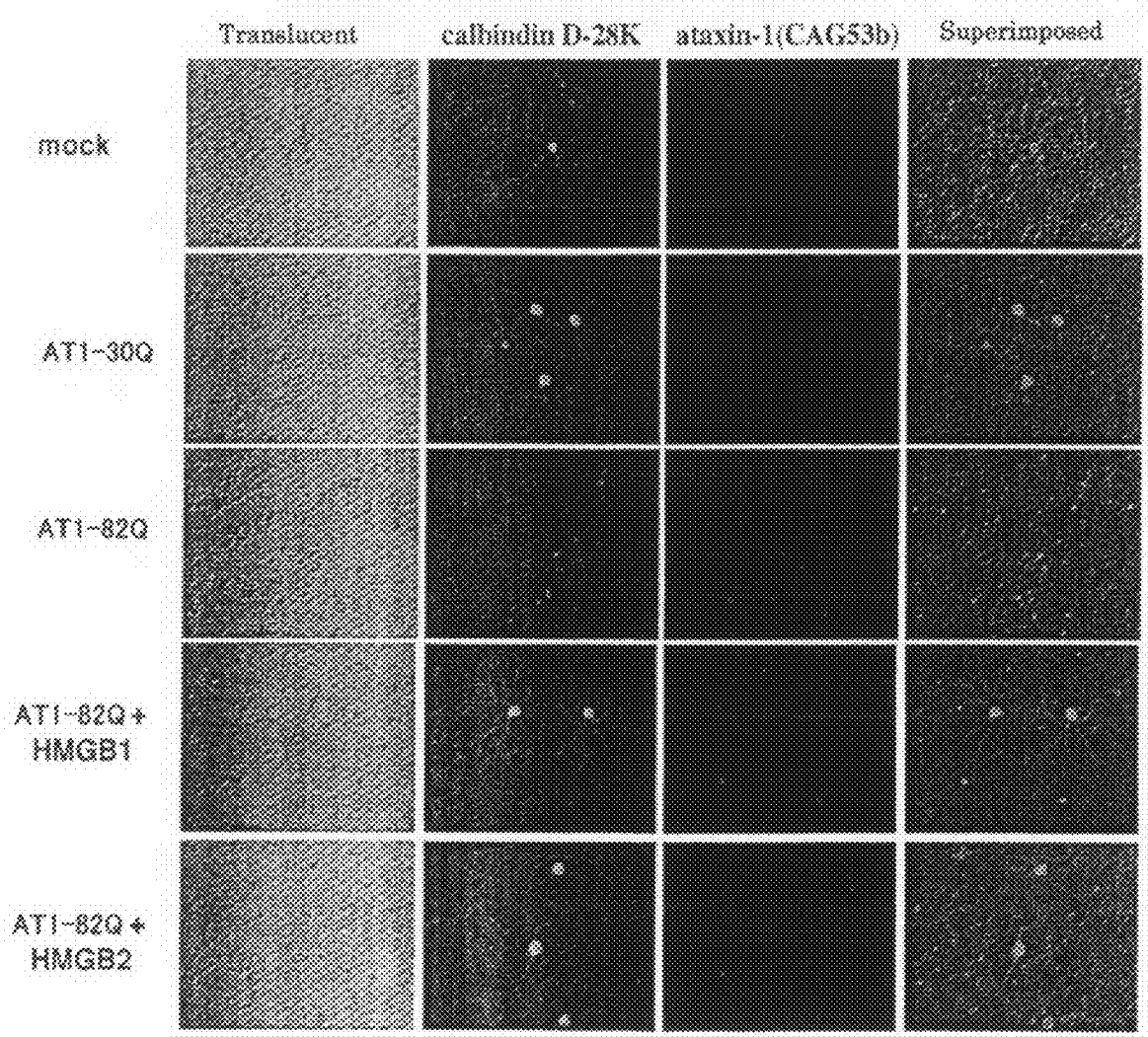
FIG. 9A shows the degree of survival and neurite extension of Purkinje cells stained with anti-calbindin 28K antibody and measured using Aquacosmos (HAMAMATSU).
Figure 9B:
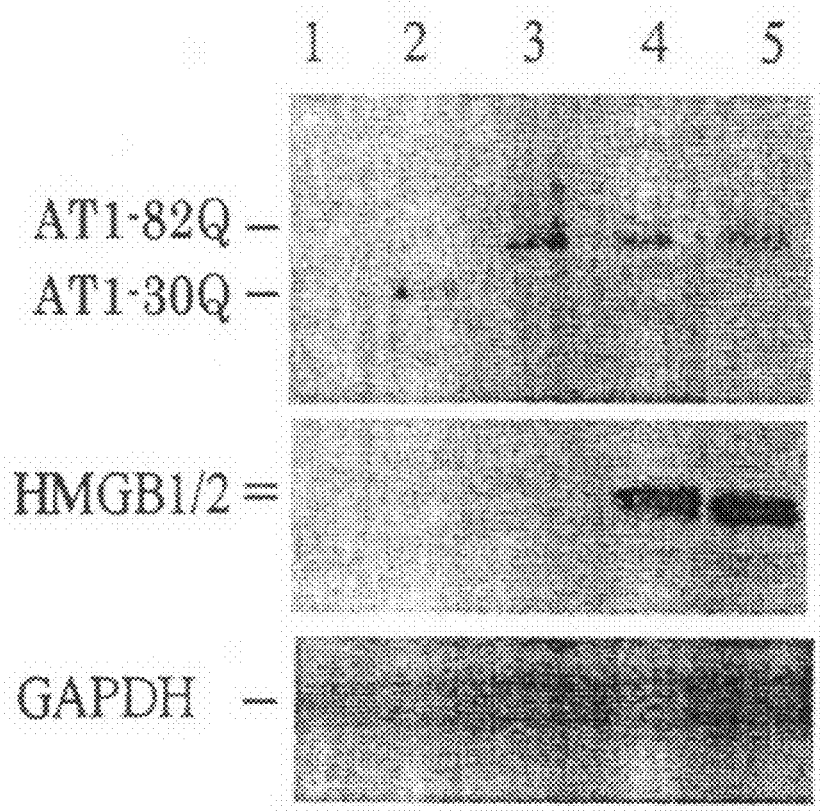
FIG. 9B shows the results of Western blot confirming the expression levels of AT1 and HMGB proteins in infected primary cortical neurons.
Figure 10A:
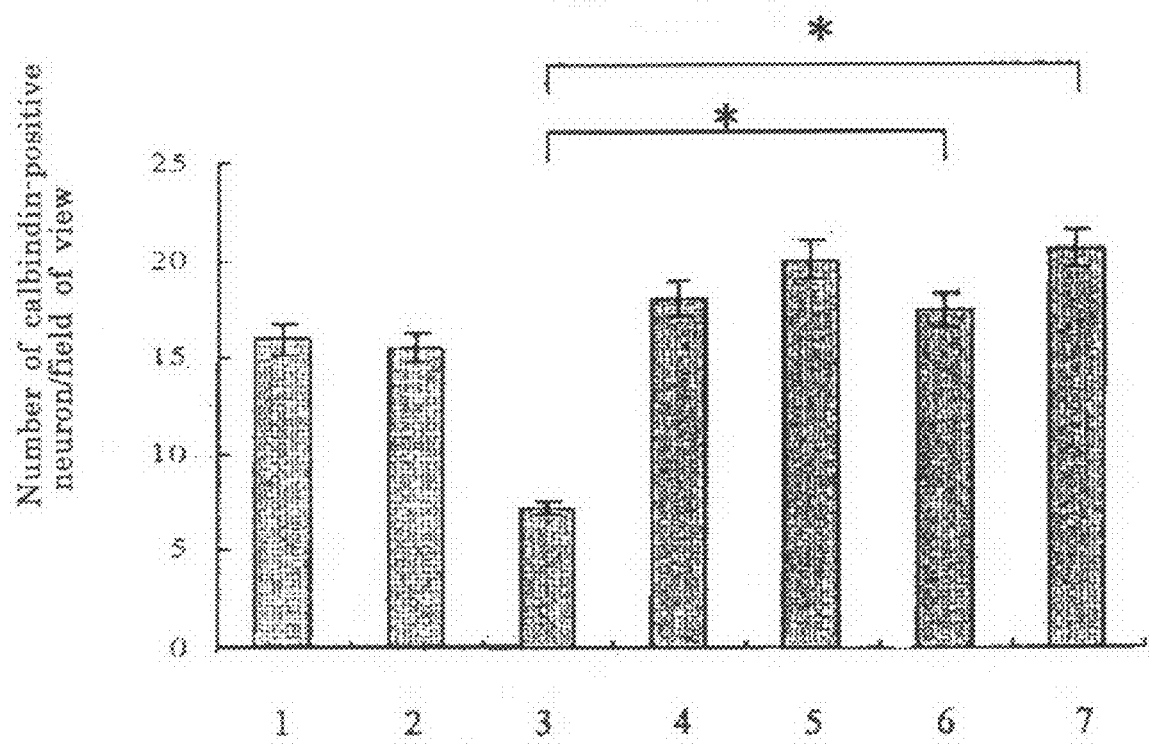
FIG. 10A shows the results of quantitative analysis of the survival of Purkinje cells.
Figure 10B:
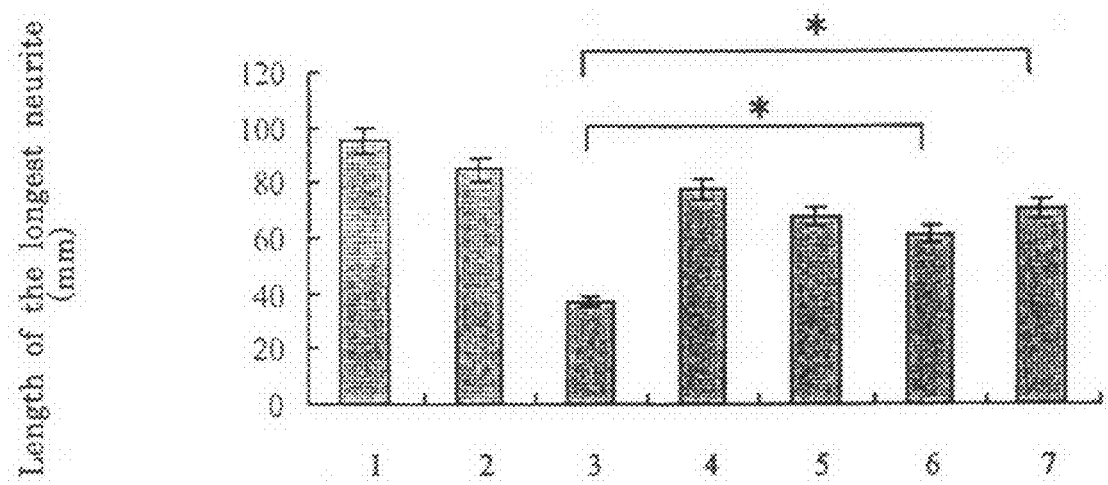
FIG. 10B shows the results of quantitative analysis of the neurite extension of Purkinje cells.

The effect of HMGB proteins on the AT1-induced toxicity in brain neurons was tested. The effect was examined in Purkinje cells since mutant AT1 did not induce cell death of granular neurons, as expected from the human SCA1 pathology. Mutant AT1 hindered the survival, neurite extension and neurite branching of Purkinje cells (FIG. 9A, AT1-82Q). In contrast, AxCA and AxCA-AT1-30Q viruses did not affect Purkinje cells significantly (mock, AT1-30Q). HMGB1 and 2 proteins reduced the toxicity of mutant AT1 against the survival, neurite extension and neurite branching of Purkinje cells (FIG. 9A, AT1-82Q+HMGB1AT1-82Q+HMGB2) ($p<0.01$) (FIG. 10A, 10B, 10C). As in the AT1 knock-in mouse and SCA1 human pathology, no inclusion body was observed in Purkinje cells, as opposed to what was seen in granulocytes (FIG. 9A). However, the expression of AT1 and HMGB proteins was confirmed (FIG. 9B). Similar experiments were conducted using primary cerebral neurons prepared from newborn AT1 knock-in mice. Similar advantageous effect was brought about by HMGB proteins, though not statistically significant. This is due to the extremely low toxicity of mutant AT1 in the cerebral neurons of the newborn mice that have not developed any symptoms. In FIG. 9A, Purkinje cells were stained with anti-calbindin 28K antibody and the survival and neurite extension were measured using Aquacosmos (HAMAMATSU). FIG. 9B shows the results of Western blot confirming the expression levels of AT1 and HMGB proteins in the infected primary cortical neurons. In FIG. 9B, Lane 1 is the result of AxCA infection; Lane 2 is the result of AxCA-AT1-30Q infection; Lane 3 is the result of AxCA-AT1-82Q infection; Lane 4 is the result of AxCA-AT1-82Q and AxCA-HMGB1 infection; and Lane 5 is the result of AxCA-AT1-82Q and AxCA-HMGB2 infection. FIG. 10A shows the results of quantitative analysis of the survival of Purkinje cells obtained for 20 fields of view (*: $p<0.01$, Student t-test). FIG. 10B shows the results of quantitative analysis of the neurite extension of Purkinje cells in which 50 or more Purkinje cells were examined for each infection except for AxCA-AT1-82Q (n=20) (*: $p<0.01$, Student t-test). FIG. 10C shows the results of quantitative analysis of the neurite branching of Purkinje cells in which 50 or more Purkinje cells were examined for each infection except for AxCA-AT1-82Q (n=20) (*: $p<0.01$, Student t-test). In FIGS. 10A, 10B, and 10C, Lane 1 is the result of AxCA and AxCA co-infection; Lane 2 is the result of AxCA-AT1-30Q and AxCA co-infection; Lane 3 is the result of AxCA-AT1-82Q and AxCA co-infection; Lane 4 is the result of AxCA-HMGB1 and AxCA co-infection; Lane 5 is the result of AxCA-HMGB2 and AxCA co-infection; Lane 6 is the result of AxCA-AT1-82Q and AxCA-HMGB1 co-infection; and Lane 7 is the result of AxCA-AT1-82Q and AxCA-HMGB2 co-infection.

Figure 11A:
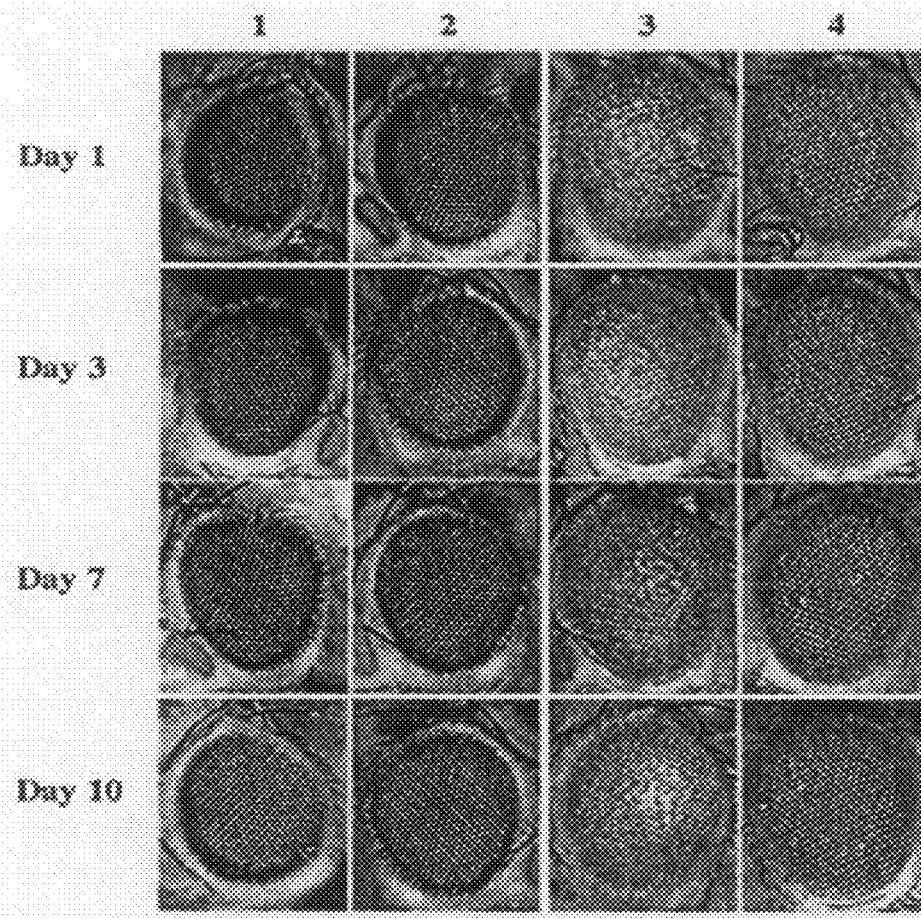
FIG. 11A shows the results of light microscopy and electron microscopy of the eye degeneration in a Drosophila strain expressing mutant AT1 at days 1 to 10.
Figure 11B:
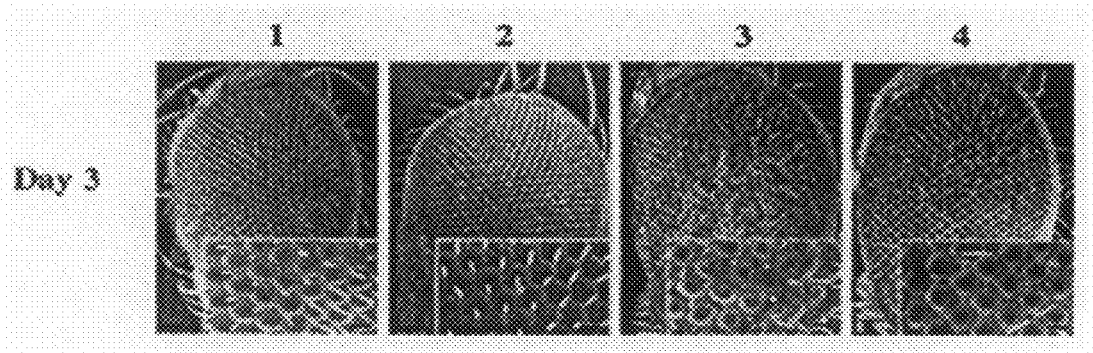
FIG. 11B shows the enlarged electron microscopy of the eye degeneration in a Drosophila strain expressing mutant AT1 at day 3.

To further investigate the protective effect of HMGB proteins against the polyglutamine toxicity, HMGB1 protein transgenic Drosophila were created and crossed with Drosophila strains expressing human mutant AT1 and Htt (Fernandez-Funez, P. et al., Nature 408, 1001-106 (2000); Jackson, G. R. et. al., Neuron. 21, 633-642 (1998)). In our transgenic flies, HMGB1 protein is specifically expressed by GMR-GAL4 at the developmental stage and in adult eyes (data not shown). The eye degeneration in Drosophila strain expressing mutant AT1 was detected by light microscopy and electron microscopy for 1 to 10 days at 25° C. (FIG. 11A, 11B). Heterozygous HMGB1 (HMGB1-2.1) flies were crossed with AT1-82Q homozygous transgenic flies (F7, human AT1 gene located on X chromosome) to generate a population expressing both genes and a population expressing only AT1-82Q. Light microscopy and SEM revealed that HMGB1 suppressed neuronal degeneration by mutant AT1 in vivo. Similar effect was observed in another HMGB1 transgenic strain (HMGB1-4.1). To exclude the possibility that the expression of AT1-82Q was decreased due to the competition for GL4 protein between UAS-AT1-82Q and UAS-HMGB1-2.1, the expression of AT1-82Q was examined in two transgenic strains (UAS-AT1-82Q/X; GMR-GAL4/Cyo and UAS-AT1-82Q/X; GMR-GAL4/UAS-HMGB1-2.1). It was confirmed that AT1-82Q was equally expressed in these strains (data not shown). FIG. 11A shows the results of light microscopy and FIG. 11B shows the results of electron microscopy. In FIGS. 11A and 11B, Lane 1 is the result of X/Y; GMR-GAL4/Cyo. Lane 2 is the result of X/Y; GMR-GAL4/UAS-HMGB1-2.1. Lane 3 is the result of UAS-AT1-82Q/X; GMR-GAL4/Cyo. Lane 4 is the result of UAS-AT1-82Q/X; GMR-GAL4/UAS-HMGB1-2.1.

Figure 12A:
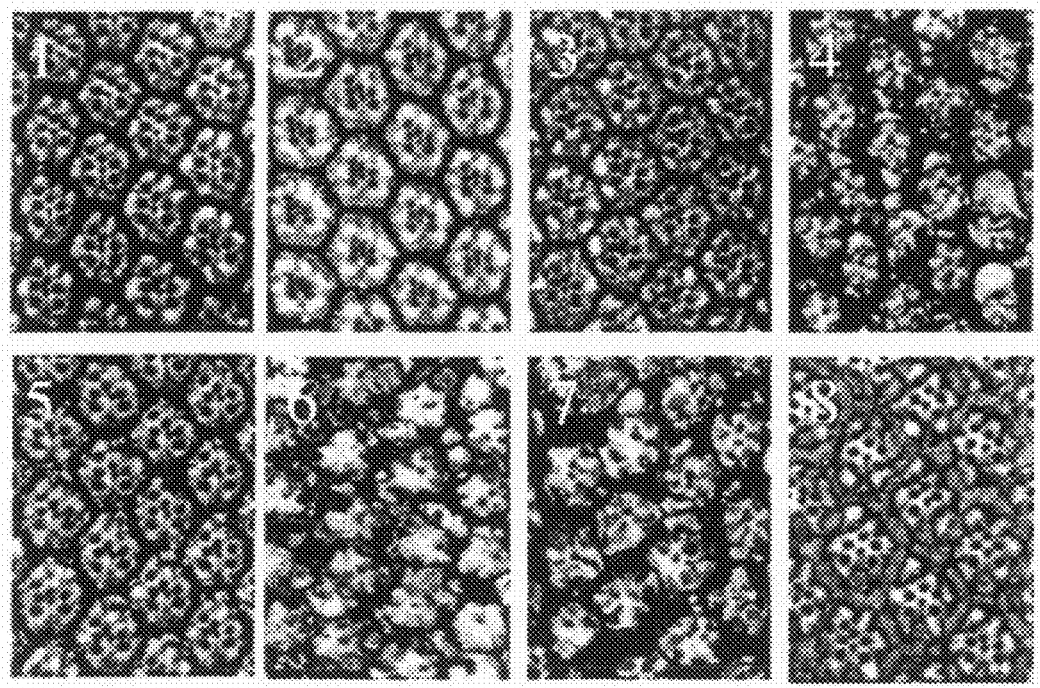
FIG. 12A shows the results of histological analysis of eye cross-section demonstrating the effect of HMGB1 on Htt-induced eye degeneration in Drosophila.
Figure 12B:
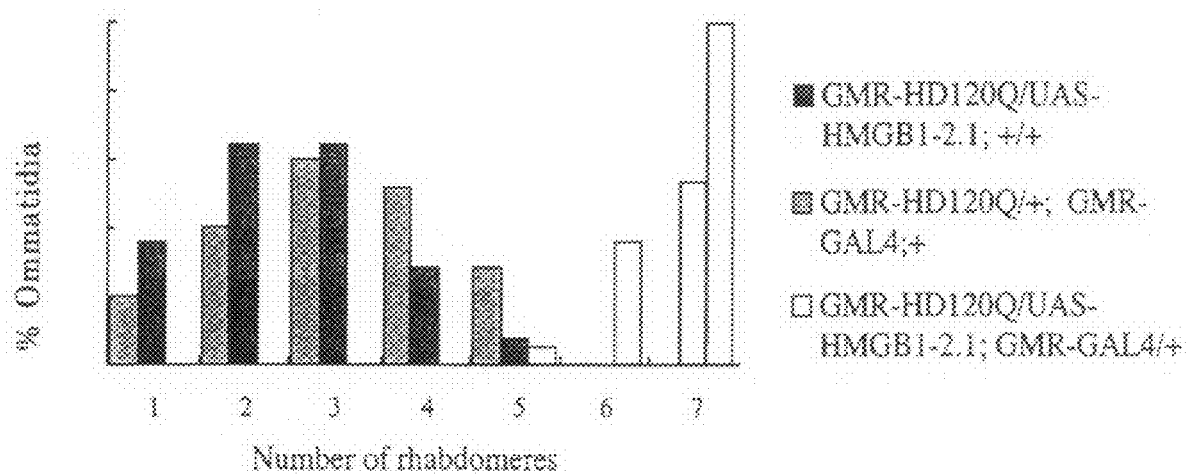
FIG. 12B shows the quantified results of FIG. 12A.

The effect of HMGB1 on the Htt-induced eye degeneration in Drosophila was observed. Since mutant Htt-transgenic flies do not exhibit rough eye phenotype (Jackson, G. R. et. al., Neuron. 21, 633-642 (1998)), the effect of HMGB1 was examined by analyzing the histology of eye cross-section. The expression of mutant Htt disrupted the structure of facets and led to the destruction of the photoreceptor cells (FIG. 12A, Panel 4). The expression of HMGB1 mitigated damage to photoreceptor neurons (FIG. 12A, Panel 8). This effect was not observed by the expression of GMR-GAL4 alone (FIG. 12A, Panel 7) or UAS-HMGB1 transgene alone (FIG. 12A, Panel 6). Quantitative analysis of the number of rhabdomere per facet supported the effect caused by the expression of HMGB1 (FIG. 12B). These results indicate that HMGB1 suppresses the polyglutamine-induced neural degeneration in Drosophila. The observation that EP-HMGD (Drosophila HMG containing an HMG box and basic/acidic regions) acts as a suppressor of AT1-induced neural degeneration and EP-DSP-1 (Drosophila protein containing two HMG boxes but lacking basic/acidic regions) acts as a promoter of the disease condition supports the role of HMGB proteins as a suppressor of polyglutamine diseases. In FIG. 12A, Panel 1 is the result of WT; Panel 2 is the result of UAS-HMGB1-2.1/+; +/+; Panel 3 is the result of +/+; GMR-GAL4/+; Panel 4 is the result of GMR-HD120Q/+; +/+; Panel 5 is the result of UAS-HMGB1-2.1/+; GMR-GAL4/+; Panel 6 is the result of GMR-HD120Q/UAS-HMGB1-2.1; +/+; Panel 7 is the result of GMR-HD120Q/+; GMR-GAL4/+; and Panel 8 is the result of GMR-HD120Q/UAS-HMGB1-2.1; GMR-GAL4/+.

What is claimed is:

1. A prophylactic/therapeutic agent for neurodegenerative disease, the agent comprising: an isolated protein comprising the amino acid sequence of SEQ ID NO: 2.

* * * * *